United States Patent
Anderson et al.

(10) Patent No.: US 10,134,296 B2
(45) Date of Patent: Nov. 20, 2018

(54) ENHANCING MOVEMENT TRAINING WITH AN AUGMENTED REALITY MIRROR

(71) Applicant: AUTODESK, INC., San Rafael, CA (US)

(72) Inventors: Fraser Anderson, Camrose (CA); Tovi Grossman, Toronto (CA); Justin Frank Matejka, Etobicoke (CA); George Fitzmaurice, Toronto (CA)

(73) Assignee: AUTODESK, INC., San Rafael, CA (US)

( * ) Notice: Subject to any disclaimer, the term of this patent is extended or adjusted under 35 U.S.C. 154(b) by 602 days.

(21) Appl. No.: 14/315,574

(22) Filed: Jun. 26, 2014

(65) Prior Publication Data

US 2015/0099252 A1    Apr. 9, 2015

Related U.S. Application Data

(60) Provisional application No. 61/886,534, filed on Oct. 3, 2013.

(51) Int. Cl.
*G09B 5/02* (2006.01)
*G09B 19/00* (2006.01)
(Continued)

(52) U.S. Cl.
CPC ............ *G09B 5/02* (2013.01); *G06F 19/3481* (2013.01); *G06K 9/00342* (2013.01);
(Continued)

(58) Field of Classification Search
CPC ............ G09B 19/003; A63B 2220/803; A63B 2220/16; A63B 2024/0025
(Continued)

(56) References Cited

U.S. PATENT DOCUMENTS 5,142,562 A * 8/1992 Guichard ............... H04N 7/142
                                                            348/14.01
5,344,323 A * 9/1994 Burns .................... A63B 69/00
                                                            434/247
(Continued)

OTHER PUBLICATIONS

Anderson et al. "You Move: Enhancing Movement Training with an augmented Mirror", UIST'13, Oct. 8-11, 2013, Vision, St. Andrews, UK.*

*Primary Examiner* — James Hull
*Assistant Examiner* — Sadaruz Zaman
(74) *Attorney, Agent, or Firm* — Artegis Law Group, LLP

(57) ABSTRACT

One embodiment of the invention disclosed herein provides techniques for controlling a movement training environment. A movement training system retrieves a movement object from a set of movement objects. The movement training system attains first motion capture data associated with a first user performing a movement based on the movement object. The movement training system generates a first articulable representation based on the first motion capture data. The movement training system compares at least one first joint position related to the first articulable representation with at least one second joint position related to a second articulable representation associated with the movement object. The movement training system calculates a first similarity score based on a difference between the at least one first joint position and the at least one second joint position.

20 Claims, 16 Drawing Sheets

(51) Int. Cl.
    *G06F 19/00*     (2018.01)
    *G06K 9/00*     (2006.01)
    *G06T 7/00*     (2017.01)
    *G06T 11/00*     (2006.01)
    *G06T 7/246*     (2017.01)

(52) U.S. Cl.
    CPC ............ *G06T 7/0014* (2013.01); *G06T 7/251* (2017.01); *G06T 11/00* (2013.01); *G09B 19/003* (2013.01); *G06T 2207/30196* (2013.01); *G06T 2207/30221* (2013.01)

(58) Field of Classification Search
    USPC .......................................................... 434/258
    See application file for complete search history.

(56) References Cited

U.S. PATENT DOCUMENTS

| | | | | |
|---|---|---|---|---|
| 5,554,033 A * | 9/1996 | Bizzi | ................. | A63B 24/0006 434/247 |
| 5,846,086 A * | 12/1998 | Bizzi | ................. | A63B 24/0006 434/247 |
| 9,088,787 B1 * | 7/2015 | Smith | ................ | H04N 13/0278 |
| 2004/0219498 A1 * | 11/2004 | Davidson | ............... | A63B 69/00 434/247 |
| 2006/0103627 A1 * | 5/2006 | Watanabe | .............. | G03B 21/10 345/156 |
| 2007/0165155 A1 * | 7/2007 | Yang | .................... | G02B 6/0006 349/62 |
| 2007/0289784 A1 * | 12/2007 | Lapstun | ................ | G06F 3/03545 178/18.03 |
| 2008/0214360 A1 * | 9/2008 | Stirling | ................ | A61B 5/1038 482/9 |
| 2010/0157291 A1 * | 6/2010 | Kiesel | ................ | G01N 15/1429 356/244 |
| 2010/0173276 A1 * | 7/2010 | Vasin | ................ | A63B 24/0006 434/307 R |
| 2011/0210105 A1 * | 9/2011 | Romashko | ......... | B23K 26/0732 219/121.72 |
| 2012/0206577 A1 * | 8/2012 | Guckenberger | ........ | G06T 11/00 348/47 |
| 2012/0293557 A1 * | 11/2012 | Hsu | ....................... | G06F 3/0425 345/672 |
| 2013/0171596 A1 * | 7/2013 | French | ............... | G09B 19/0038 434/236 |
| 2014/0096010 A1 * | 4/2014 | Grosz | ................... | G06F 3/1242 715/733 |
| 2014/0188009 A1 * | 7/2014 | Lange | ................. | A61B 5/1128 600/595 |
| 2014/0362052 A1 * | 12/2014 | McCaughan | ........ | G06F 3/0418 345/175 |

\* cited by examiner

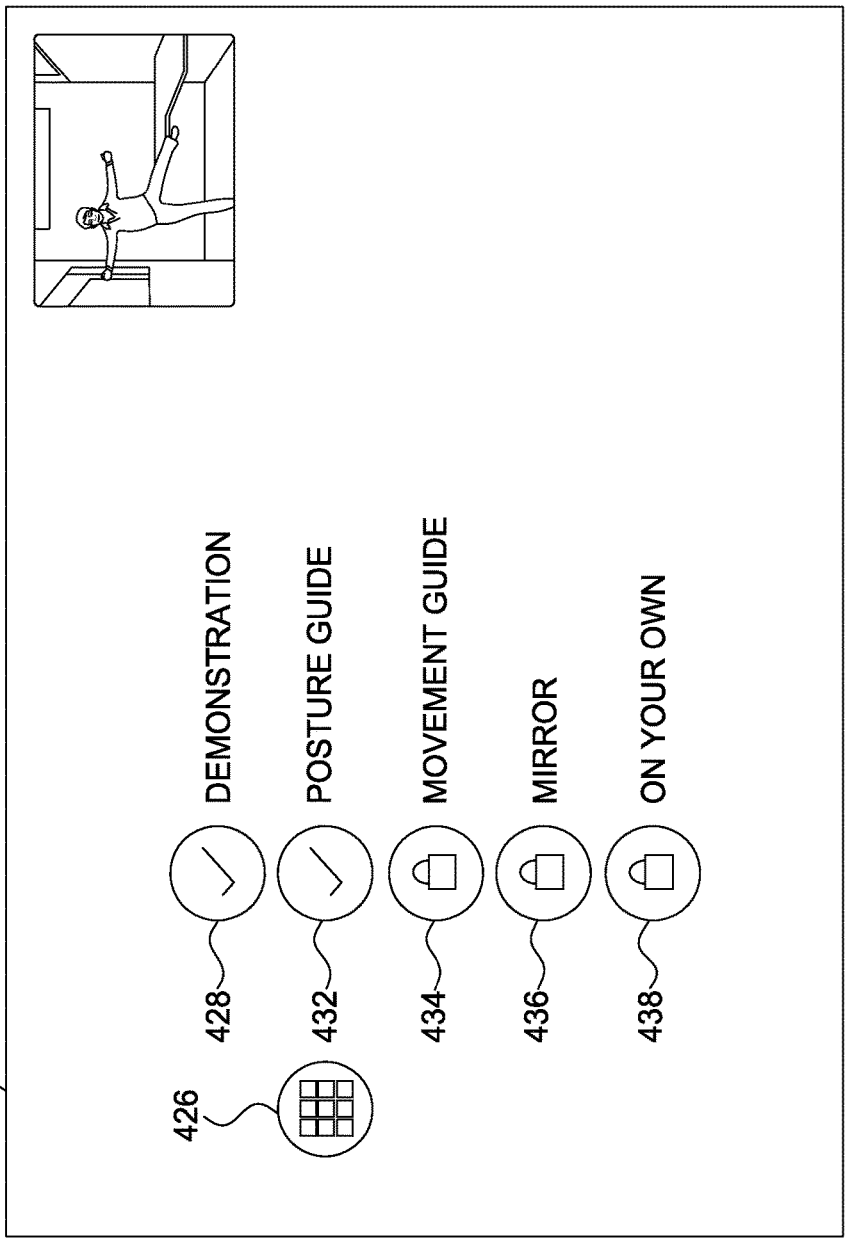

ENHANCING MOVEMENT TRAINING WITH AN AUGMENTED REALITY MIRROR

CROSS-REFERENCE TO RELATED APPLICATIONS

This application claims the benefit of United States provisional patent application entitled "YOUMOVE: ENHANCING MOVEMENT TRAINING WITH AN AUGMENTED REALITY MIRROR," Ser. No. 61/886,534, filed Oct. 3, 2013, which is hereby incorporated herein by reference.

BACKGROUND OF THE INVENTION

Field of the Invention

The present invention relates generally to augmented reality and motor learning and, more specifically, to enhanced movement training with an augmented reality mirror.

Description of the Related Art

Students learning new movements often benefit from guidance and feedback received from a live instructor. The instructor guides students verbally by giving instruction and corrective feedback. The instructor also teaches by example by performing the new movements as students watch and repeat the movements made by the instruction. Through such instruction by voice and example, students learn new movements by listening and repeating the movements of the instructor. Additionally, some movement learning environments, such as dance and martial arts studios, include one or more walls with large mirrors where the student may observe his or her own movements as well as the instructor's movements. By simultaneously observing his or her own reflection and watching the instructor, the student may learn by self-correcting his or her own movements to match the movements of the instructor.

One drawback of live instruction is that live instruction may be expensive and live instructors may not be available at a time and place that is convenient for the students. Such availability issues may hinder a student's learning progress. A potential solution to this problem could include watching pre-recorded instruction videos on a large display via some medium, such as video tape, DVD, web-based streaming, or other video source. But these approaches typically are much less interactive than live instruction. To perform typical functions, such as repeating a movement or instruction segment, or navigating to a new instruction segment, students are often encumbered with using a remote control and on-screen menus or a traditional human-computer interface, such as keyboard and mouse, thus disrupting the movement learning process.

As the foregoing illustrates, what is needed is a more effective way for students to learn new movements.

SUMMARY OF THE INVENTION

One embodiment of the present application sets forth a method for controlling a movement training environment. The method includes retrieving a movement object from a set of movement objects. The method further includes attaining first motion capture data associated with a first user performing a movement based on the movement object. The method further includes generating a first articulable representation based on the first motion capture data. The method further includes comparing at least one first joint position related to the first articulable representation with at least one second joint position related to a second articulable representation associated with the movement object. The method further includes calculating a first similarity score based on a difference between the at least one first joint position and the at least one second joint position.

Other embodiments include, without limitation, a computer-readable medium that includes instructions that enable a processing unit to implement one or more aspects of the disclosed methods. Other embodiments include, without limitation, a subsystem that includes a processing unit configured to implement one or more aspects of the disclosed methods as well as a computing system configured to implement one or more aspects of the disclosed methods.

One advantage of the disclosed techniques is that users learn new movements interactively without the need for live instruction and without the limitations of other remote training approaches. Users may quickly navigate to different movements, different training stages, phases, or modules for a particular movement, and different keyframes of the movement to focus training where most needed. As a result, trainees may increase proficiency more quickly than with other remote movement learning techniques.

BRIEF DESCRIPTION OF THE DRAWINGS

So that the manner in which the above recited features of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 4C training module selection user-interface screen, according to one embodiment of the present invention;

DETAILED DESCRIPTION

In the following description, numerous specific details are set forth to provide a more thorough understanding of the present invention. However, it will be apparent to one of skill in the art that embodiments of the present invention may be practiced without one or more of these specific details.

Among other things, embodiments of the present invention are directed towards an approach for creating, sharing, and implemented training content via an augmented reality configured mirror. In various embodiments, a recording system enables a user to create and share training content, and a training system enables a person to use recorded data to train himself or herself in front of an augmented reality mirror in movements reflected in the recorded data. Also included is an approach for populating and querying a database of motion capture movements.

Hardware Overview

Figure 1:
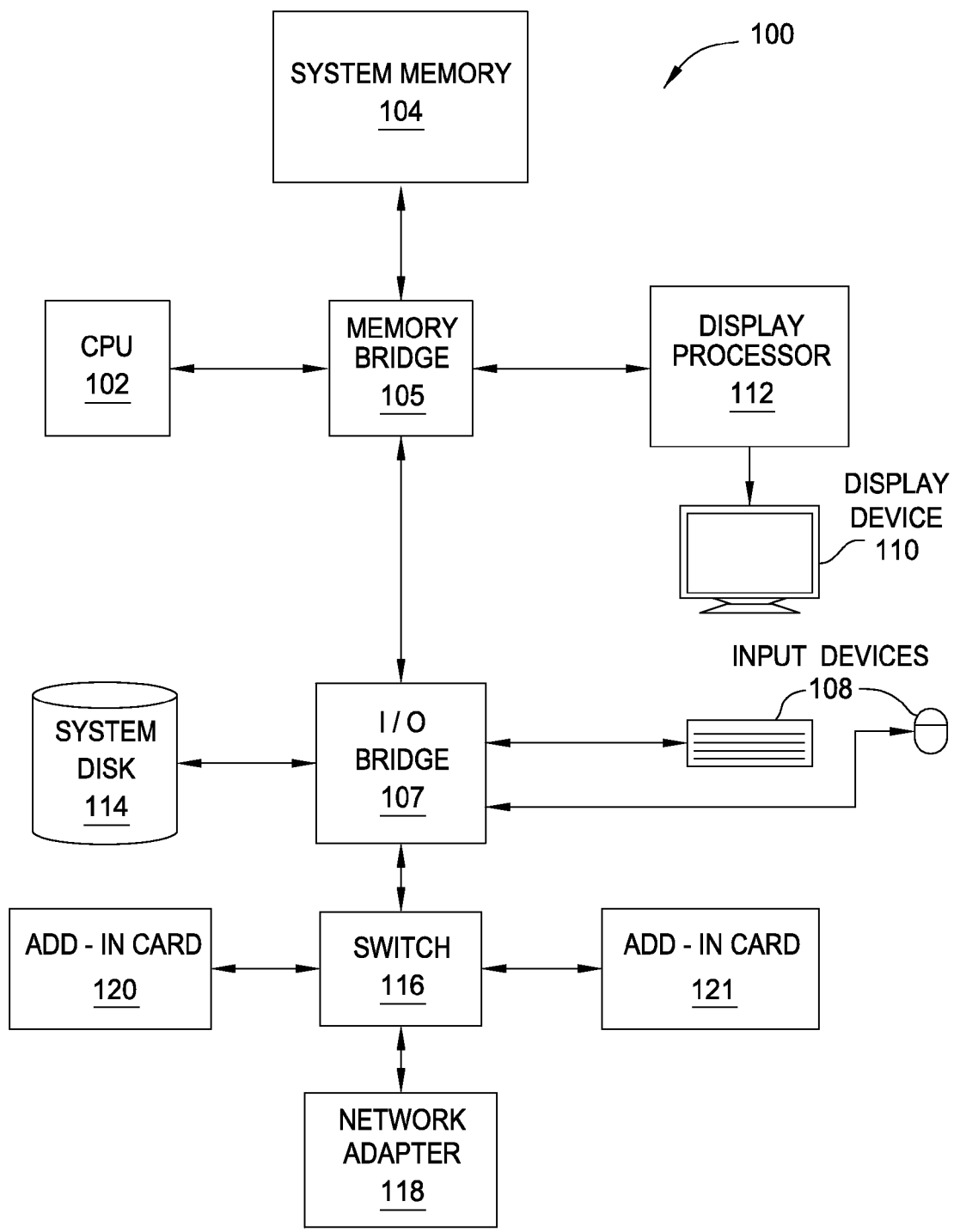
FIG. 1 is a block diagram illustrating a computer system configured to implement one or more aspects of the present invention.

FIG. 1 is a block diagram illustrating a computer system 100 configured to implement one or more aspects of the present invention. This figure in no way limits or is intended to limit the scope of the present invention. System 100 may be a personal computer, video game console, personal digital assistant, mobile phone, mobile device or any other device suitable for practicing one or more embodiments of the present invention.

As shown, system 100 includes a central processing unit (CPU) 102 and a system memory 104 communicating via a bus path that may include a memory bridge 105. CPU 102 includes one or more processing cores, and, in operation, CPU 102 is the master processor of system 100, controlling and coordinating operations of other system components. System memory 104 stores software applications and data for use by CPU 102. CPU 102 runs software applications and optionally an operating system. Memory bridge 105, which may be, e.g., a Northbridge chip, is connected via a bus or other communication path (e.g., a HyperTransport link) to an I/O (input/output) bridge 107. I/O bridge 107, which may be, e.g., a Southbridge chip, receives user input from one or more user input devices 108 (e.g., keyboard, mouse, joystick, digitizer tablets, touch pads, touch screens, still or video cameras, motion sensors, and/or microphones) and forwards the input to CPU 102 via memory bridge 105.

A display processor 112 is coupled to memory bridge 105 via a bus or other communication path (e.g., a PCI Express, Accelerated Graphics Port, or HyperTransport link); in one embodiment display processor 112 is a graphics subsystem that includes at least one graphics processing unit (GPU) and graphics memory. Graphics memory includes a display memory (e.g., a frame buffer) used for storing pixel data for each pixel of an output image. Graphics memory can be integrated in the same device as the GPU, connected as a separate device with the GPU, and/or implemented within system memory 104.

Display processor 112 periodically delivers pixels to a display device 110 (e.g., a screen or conventional CRT, plasma, OLED, SED or LCD based monitor or television). Additionally, display processor 112 may output pixels to film recorders adapted to reproduce computer generated images on photographic film. Display processor 112 can provide display device 110 with an analog or digital signal.

A system disk 114 is also connected to I/O bridge 107 and may be configured to store content and applications and data for use by CPU 102 and display processor 112. System disk 114 provides non-volatile storage for applications and data and may include fixed or removable hard disk drives, flash memory devices, and CD-ROM, DVD-ROM, Blu-ray, HD-DVD, or other magnetic, optical, or solid state storage devices.

A switch 116 provides connections between I/O bridge 107 and other components such as a network adapter 118 and various add-in cards 120 and 121. Network adapter 118 allows system 100 to communicate with other systems via an electronic communications network, and may include wired or wireless communication over local area networks and wide area networks such as the Internet.

Other components (not shown), including USB or other port connections, film recording devices, and the like, may also be connected to I/O bridge 107. For example, an audio processor may be used to generate analog or digital audio output from instructions and/or data provided by CPU 102, system memory 104, or system disk 114. Communication paths interconnecting the various components in FIG. 1 may be implemented using any suitable protocols, such as PCI (Peripheral Component Interconnect), PCI Express (PCI-E), AGP (Accelerated Graphics Port), HyperTransport, or any other bus or point-to-point communication protocol(s), and connections between different devices may use different protocols, as is known in the art.

In one embodiment, display processor 112 incorporates circuitry optimized for graphics and video processing, including, for example, video output circuitry, and constitutes a graphics processing unit (GPU). In another embodiment, display processor 112 incorporates circuitry optimized for general purpose processing. In yet another embodiment, display processor 112 may be integrated with one or more other system elements, such as the memory bridge 105, CPU 102, and I/O bridge 107 to form a system on chip (SoC). In still further embodiments, display processor 112 is omitted and software executed by CPU 102 performs the functions of display processor 112.

Pixel data can be provided to display processor 112 directly from CPU 102. In some embodiments of the present invention, instructions and/or data representing a scene are provided to a render farm or a set of server computers, each similar to system 100, via network adapter 118 or system disk 114. The render farm generates one or more rendered images of the scene using the provided instructions and/or data. These rendered images may be stored on computer-readable media in a digital format and optionally returned to system 100 for display. Similarly, stereo image pairs processed by display processor 112 may be output to other systems for display, stored in system disk 114, or stored on computer-readable media in a digital format.

Alternatively, CPU 102 provides display processor 112 with data and/or instructions defining the desired output images, from which display processor 112 generates the pixel data of one or more output images, including characterizing and/or adjusting the offset between stereo image pairs. The data and/or instructions defining the desired output images can be stored in system memory 104 or graphics memory within display processor 112. In an embodiment, display processor 112 includes 3D rendering capabilities for generating pixel data for output images from instructions and data defining the geometry, lighting shading, texturing, motion, and/or camera parameters for a scene. Display processor 112 can further include one or more programmable execution units capable of executing shader programs, tone mapping programs, and the like.

CPU 102, render farm, and/or display processor 112 can employ any surface or volume rendering technique known in the art to create one or more rendered images from the provided data and instructions, including rasterization, scanline rendering REYES or micropolygon rendering, ray casting, ray tracing, image-based rendering techniques, and/or combinations of these and any other rendering or image processing techniques known in the art.

It will be appreciated that the system shown herein is illustrative and that variations and modifications are possible. The connection topology, including the number and arrangement of bridges, may be modified as desired. For instance, in some embodiments, system memory 104 is connected to CPU 102 directly rather than through a bridge, and other devices communicate with system memory 104 via memory bridge 105 and CPU 102. In other alternative topologies display processor 112 is connected to I/O bridge 107 or directly to CPU 102, rather than to memory bridge 105. In still other embodiments, I/O bridge 107 and memory bridge 105 might be integrated into a single chip. The particular components shown herein are optional; for instance, any number of add-in cards or peripheral devices might be supported. In some embodiments, switch 116 is eliminated, and network adapter 118 and add-in cards 120, 121 connect directly to I/O bridge 107.

Movement Training System

Figure 2:
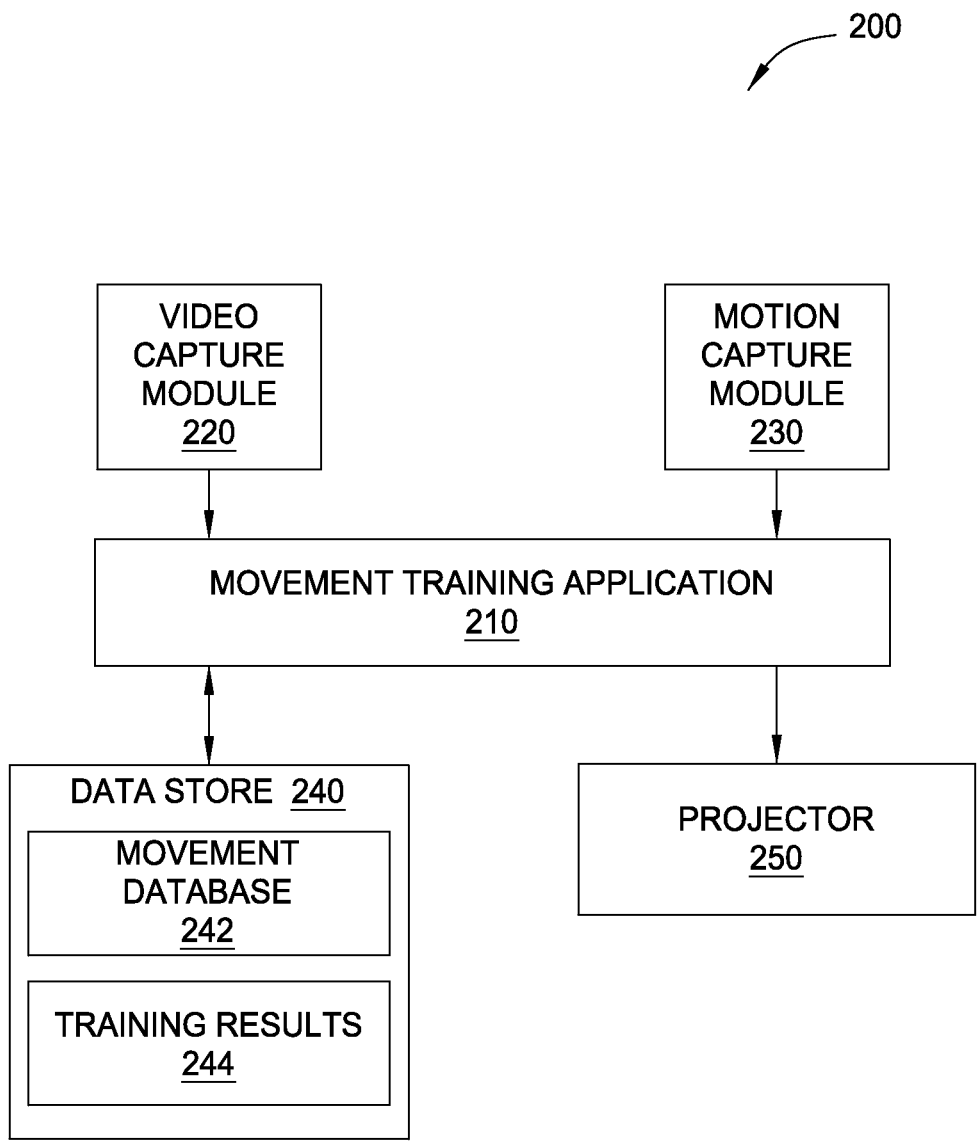
FIG. 2 is a block diagram of a movement training system, according to one embodiment of the present invention.

FIG. 2 is a block diagram of a movement training system 200, according to one embodiment of the present invention. In one embodiment, the movement training system 200 may implement the computer system 100 of FIG. 1. As shown, the movement training system 200 includes a movement training application 210, video capture module 220, a motion tracking module 225, a user-interface 230, a data store 240, and a projector 250.

The movement training application 210 is a software application executing on the movement training system 200 that facilitates authoring of movements by users, known as authors, and training of other users, known as trainees, in learning the authored movements.

The video capture module 220 transmits video information to the movement training application 210. The video information may be video of an author performing a movement for editing and storing for training purposes. Alternatively, the video information may be video of a trainee performing an authored movement, so that the trainee may view the video of the trainee along with the previously store video of the author. The trainee may then visually compare the two videos to assess the trainee's progress.

The motion tracking module 230 transmits motion information to the movement training application 210. The motion information may be motion of an author performing a movement for editing and storing for training purposes. Alternatively, the motion information may be video of a trainee performing an authored movement. The movement training application 210 compares motion information of the author with motion information of the trainee to assess the trainee's progress and compute a progress score. The movement training application 210 may create articulable skeletal representations, also referred to herein as skeletal representations, of the movement data of the author and trainee, thereby creating "stick figures." The stick figure of the author may be overlaid with the stick figure of the trainee, so that the trainee may compare his or her movement or posture with the corresponding movement or posture of the author. Finally, the motion tracking data may be associated with a user accessing a user-interface component by, for example, holding a hand in a certain position or performing a particular gesture. In this way, motion tracking data may be used as an input device for the movement training application 210.

The data store 240 receives information from the movement training application 210 for long term storage. As shown, the data store 240 includes a movement database 242 and training results 244. The movement database 242 includes movement objects, referred to herein as movements, authored by one or more users, where a movement includes, without limitation, video data, motion tracking data, keyframe data, and annotation data related to a movement performed by an author, as further described herein. One or more trainees access the movements stored in the movement database 242 to learn the authored movements. The training results 244 include progress results for one or more trainees. The training results 244 include data for each movement that a user has selected for training, including, without limitation, a score for the movement as calculated by the movement training system 200, motion tracking data of the user performing the movement, and the last module completed by the user for the movement.

The projector 250 receives images from the movement training application 210, where the images include, without limitation, user-interface components, video of the author and trainee captured by the video capture module, and movement information of the author and trainee captured by the motion tracking module 230. The projector 250 projects the received images onto an augmented reality mirror, as further described below.

Movement Training Environment

Figure 3:
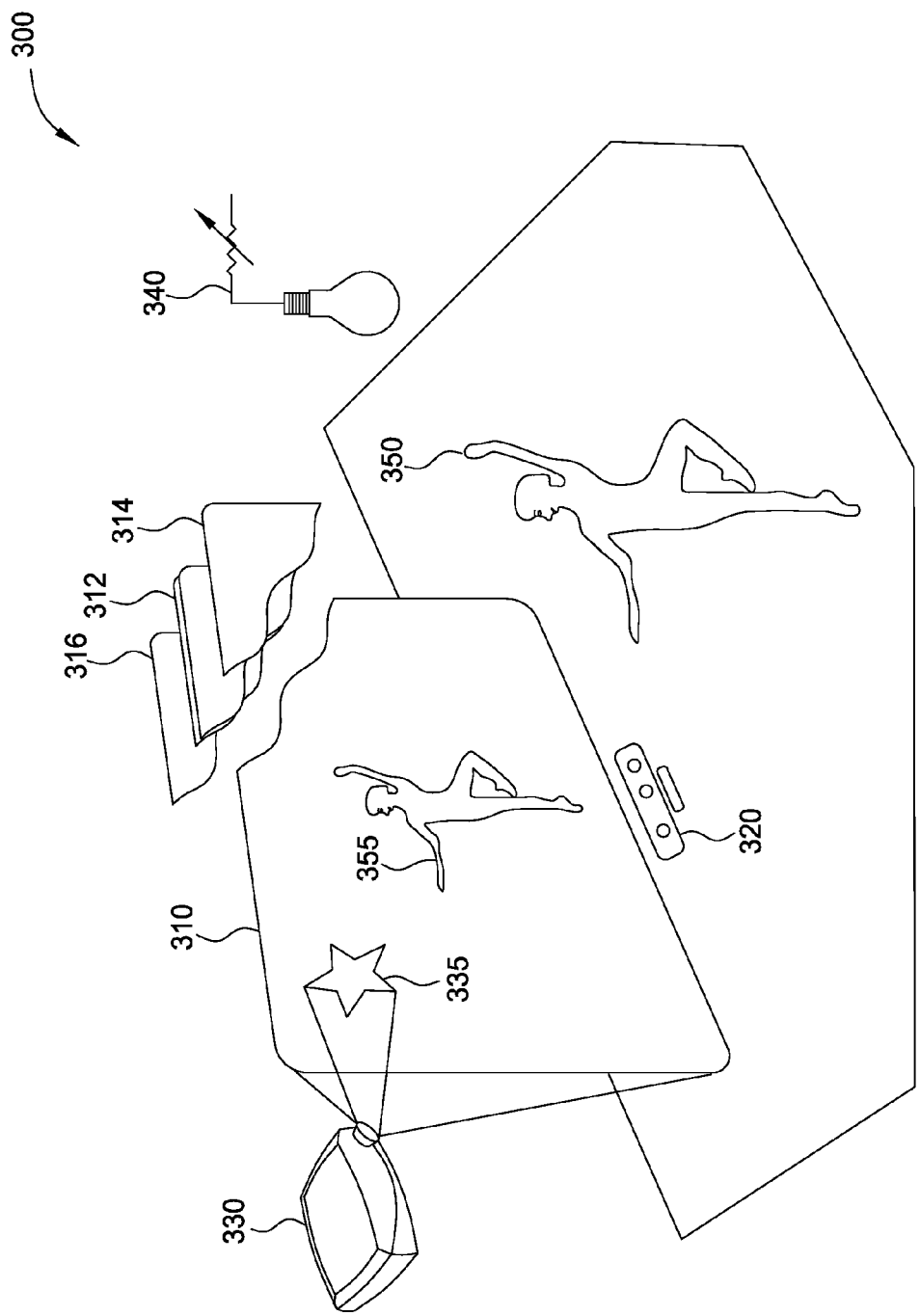
FIG. 3 illustrates a movement training environment, according to one embodiment of the present invention.

FIG. 3 illustrates a movement training environment 300, according to one embodiment of the present invention. As shown, the movement training environment 300 includes an augmented reality mirror 310, a motion tracking unit 320, a projector 330, and a dimmable light source 340.

The augmented reality mirror 310 is a large-format mirror configured to display a reflection 355 of a user 350, while simultaneously displaying interactive content 335. The user 350 sees his or her reflection 355 "overlaid" with the interactive content 335 on the surface of the augmented reality mirror 310. The augmented reality mirror 310 approximates the size and functionality of floor-to-ceiling mirrors, such as the mirrors typically deployed in dance studios, with the addition of interactive content 335. The augmented reality mirror 310 includes a pane of glass 312 with a half-silvered mirror film 314 applied to one side of the pane of glass 312 and a diffusion film 316 applied to the other side of the pane of glass 312.

The half-silvered mirror film 314 is applied to the surface of the pane of glass 312 that faces the user 350. In one embodiment, the half-silvered mirror film 314 is configured to transmit between about 10-35% of the visible light and to reflect between about 50-60% of the visible light. In another embodiment, the half-silvered mirror film 314 is configured to absorb approximately 25% of the visible light. In a specific embodiment, the half-silvered mirror film 314 is configured to transmit approximately 16% of the visible light and to reflect approximately 58% of the visible light. The diffusion film 316 is configured to diffuse the light projected from a rear-mounted projector 330 that projects an image onto the surface of the diffusion film 316. The resulting augmented reality mirror 310 provides a reflective surface that allows projected light to pass through. Mirror films that have transmission and reflection values outside of the value ranges set forth above for the half-silvered mirror film 314 may absorb an excessive amount of the projected light, thereby obscuring the interactive content 335 from the projector 330, or may not provide a clear reflection, thereby obscuring the image of the user 350.

The motion tracking unit 320 tracks the position of the user 350 as the user moves in front of the augmented reality mirror 310. The motion tracking unit 320 is typically mounted below and aimed in the direction of the user 350. The motion tracking unit 320 may be programmed with the location and size of the augmented reality mirror 310, within the coordinate space of the motion tracking unit 320. The motion tracking unit 320 reports the 3D coordinates of various key positions, such as joint positions, of the user 350. The motion tracking unit 320 reports these 3D coordinates multiple times per second. Typically, the augmented reality environment 300 is calibrated by specifying the location of the augmented reality mirror 310 in relation to other elements of the augmented reality environment 300 such as the motion tracking unit 320 and the projector 330. The position of a particular point on the user 350, such as the head of the user 350, along with the four corner positions of the augmented reality mirror, 310 define an asymmetric projection matrix. The movement training system 200 uses this asymmetric projection matrix to render on-screen content that overlays with the reflection 355 of the user 350 in the augmented reality mirror 310.

The projector 330 projects interactive content 335 onto the surface of the diffusion film 316 of the augmented reality mirror 310. The interactive content 335 includes, without limitation, menu selection buttons, video of the trainer or trainee performing a movement, and movement data in the form of a "stick figure." The movement data is projected onto the augmented reality mirror 310 in such a manner that the movement data overlays the reflection 355 of the actual user 350 in the augmented reality mirror 310.

The dimmable light source 340 is configured to control the ambient lighting conditions of the movement training environment 300. The dimmable light source 340 includes a servo-controlled motor mounted to a dimmer control that adjusts the position of the dimmer control, thereby manipulating the level of ambient light in the movement training environment 300. The movement training system 200 is configured to control the dimmable light source 340 via any technically feasible approach, such as via a universal serial bus (USB) interface.

If the dimmable light source 340 is controlled to provide a high level of ambient light and the projector 330 is controlled to provide a dark projection image, then the user 350 observes only his or her reflection 355 in the augmented reality mirror 310 and does not observe any interactive content 335 from the projector 330. If the dimmable light source 340 is controlled to provide a low level of ambient light and the projector 330 is controlled to provide a bright projection image, then the user 350 observes only the interactive content 335 from the projector 330 in the augmented reality mirror 310 and does not observe his or her reflection 355. If the dimmable light source 340 is controlled to provide a moderate level of ambient light and the projector 330 is controlled to provide a moderate to bright projection image, then the user 350 observes both the interactive content 335 from the projector 330 and his or her reflection 355 in the augmented reality mirror 310. By controlling the dimmable light source 340 and the projector 330, the movement training system 200 may direct the attention of the user 350 to the projected image, the reflected image, or the projected image overlaid onto the reflected image.

The user 350 interacts with the movement training environment 300 to directly activate user-interface components projected onto the augmented reality mirror 310. As a result, the user, 350 directly manipulates a 2D interface projected onto the augmented reality mirror 310 from 3D free-space. This reflection-based selection provides zero latency feedback and quick positioning based on hand position. In other words, the user 350 directly places his or her hand such that the reflection 355 of the hand intersects with the projection of the desired user-interface component. The user 350 activates a user-interface component, such as a button, by dwelling the hand over the user-interface component. During the dwell period, the button expands, showing that the button is selected, thereby providing feedback to the user 350. During the dwell period, the activation area for the button may be increased to allow for the user's hand to drift.

In some embodiments, the user-interface for the movement training environment 300 may include two button types. The first button type includes global menu buttons located on the left side of the augmented reality mirror 310. The location of the global menu buttons may be selected such that the global menu buttons are not triggered accidently during training. The vertical position of the global menu buttons may adapt to the height of the user 350, so that the global menu buttons are not out of reach. The second button type includes quick-access contextual buttons that are presented near the head of the user 350 positioned with a fixed offset relative to the reflection 355 of the user 350. The fixed offset positioning of the quick-access contextual buttons allows these buttons to be activated by a 'gesture posture,' such as a sweep of the hand in a particular direction.

Users of the movement training environment 300 may invoke various functions of the movement training system 200 via a graphical user-interface (GUI) that includes a series of user-interface screens, as further described below.

Figure 4A:
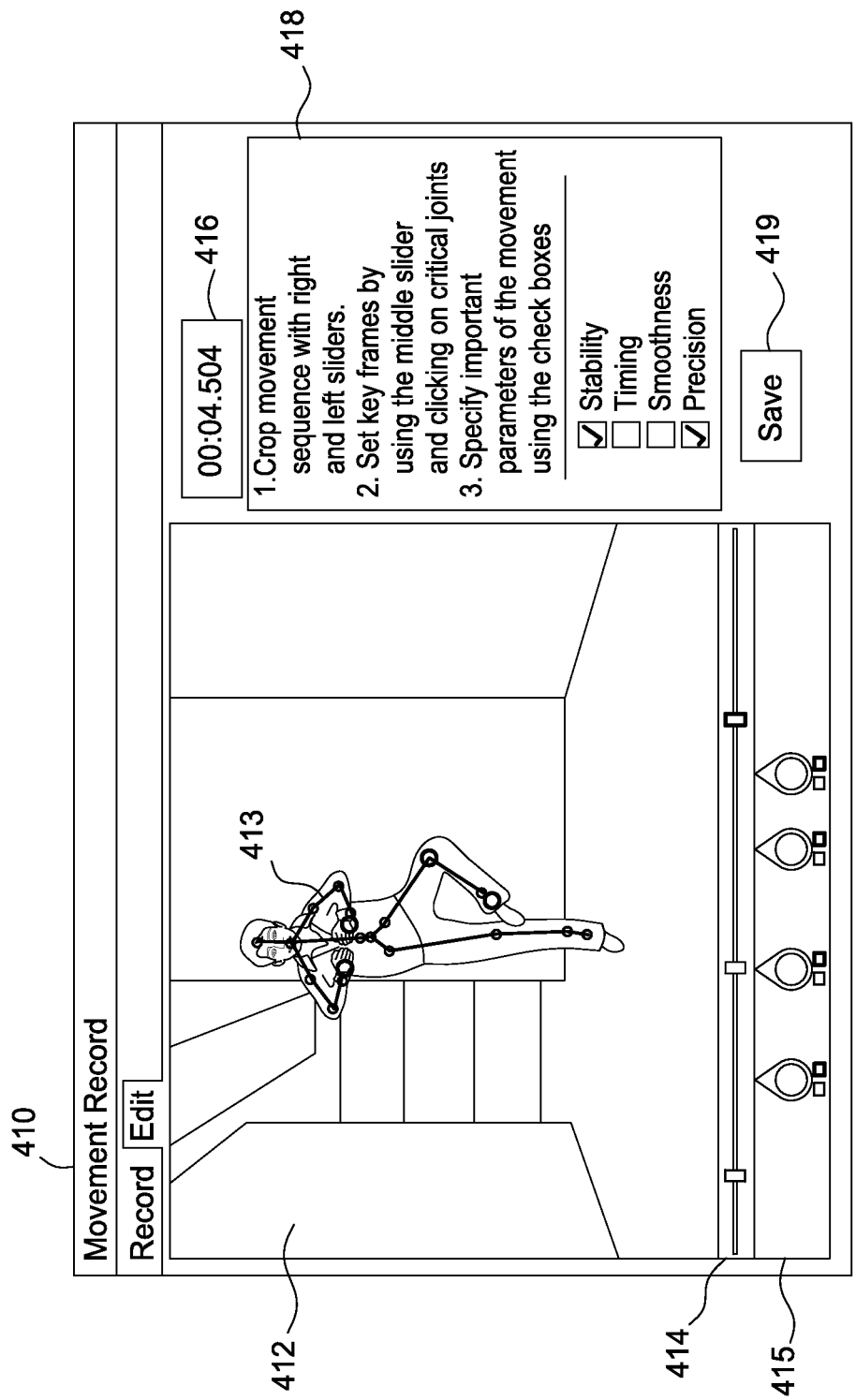
FIG. 4A illustrates a movement authoring user-interface screen, according to one embodiment of the present invention.

FIG. 4A illustrates a movement authoring user-interface screen 410, according to one embodiment of the present invention. As shown, the movement authoring user-interface screen 410 includes a video image 412, a skeletal movement representation 413, a progress bar 414, keyframe markers 415, a timecode window 416, an instruction dialog 417, and a save button 418. The user 350 who records and modifies a movement via the movement authoring user-interface screen 410 is referred to herein as an "author." Correspondingly, the user 350 who accesses a movement created by an author in order to learn the movement is referred to herein as a "trainee."

The video image 412 illustrates an image as captured by the video capture module 220. Likewise, the skeletal movement representation 413 illustrates a "stick figure" overlaid on the video image 412, where the stick figure reflects the data points identifying the locations of one or more joints of the author, as reported by the motion tracking module 225. The user 350 records a movement by activating a "Record" button (not shown), performing the movement, and then stopping the recording by pressing a "Stop" button (not shown) or by holding a final pose for a period of time without moving. During the record process, the video image 412 and the skeletal movement representation 413 reflect live capture of the image and motion tracking data of the author. After recording stops, the video image 412 and the skeletal movement representation 413 reflect the previously recorded movement. The recorded movement includes video, audio and 3D skeleton movement data of the author as he or she performs the movement.

The progress bar 414 indicates a position along a timeline corresponding to the recorded movement. As shown, the progress bar includes a left marker, a middle marker, and a right marker. The author moves the left marker and the right marker to select the portion of the recorded movement to save. By adjusting the left marker and the right marker, the author trims the recording to eliminate unwanted data at the beginning and end of the movement—such as when the author is walking prior to when the movement begins or after the movement ends. The middle marker indicates the current position within the movement, as shown by the video image 412 and the skeletal movement representation 413.

The keyframe markers 415 illustrate one or more keyframes for the recorded movement, as specified by the author. Keyframes are postures within the movement that are considered by the user as particularly important for a trainee to match when learning the movement. For example, a keyframe for a baseball throw may include the point when the hand holding the ball reaches peak extension. The author specifies a frame in the movement as a keyframe by navigating to the desired frame within the movement and then clicking on one or more joints of the skeletal movement representation 413 to specify the important joints for that keyframe. When a joint is selected, the current frame becomes a keyframe. These keyframes and important joints are used by the movement training system 200 to provide tailored guidance and feedback to a trainee. The author can also associate an additional annotation data, such as an audiovisual recording or text, with individual keyframes, allowing the trainer to provide additional information regarding the movement. This annotation is accomplished by clicking the 'record' and 'stop' buttons below each keyframe marker 415. Annotations provide information that may not be immediately obvious to a trainee from observing the author's movement, or to discuss common pitfalls to avoid. For example, to throw a baseball, an author may annotate the keyframe with a short clip explaining that the elbow should be at approximately 90 degrees at a certain point during the throw.

The timecode window 416, illustrates the time associated with the current position reflected by the video image 412, the skeletal movement representation 413, and the middle marker of the progress bar 414.

The instruction dialog 417 guides the author in creating and modifying the movement. As shown, the instruction dialog 417 instructs the author on how to trim, or crop, the movement by sliding the left marker and the right marker in the progress bar 414. Likewise, the instruction dialog 417 also instructs the author to create keyframes by moving the middle marker in the progress bar 414 and then clicking on critical joints. Finally, the instruction dialog 417 instructs the author to identify important parameters for the movement by checking boxes related to stability, timing, smoothness, and precision when performing the movement. The movement training system 200 uses these parameters when calculating a performance score or providing feedback to the trainee.

The save button 418 allows the author to save the current movement. The author saves the movement by clicking the save button 418. The data is saved as one or more media files, such as mp4 video and wav audio, and plain-text files containing time-stamped motion capture and keyframe metadata used to synchronize the movement data.

A user 350 identified as a trainee accesses the movement training system 200 to learn the movements previously recorded by one or more authors, as further described below.

Figure 4B:
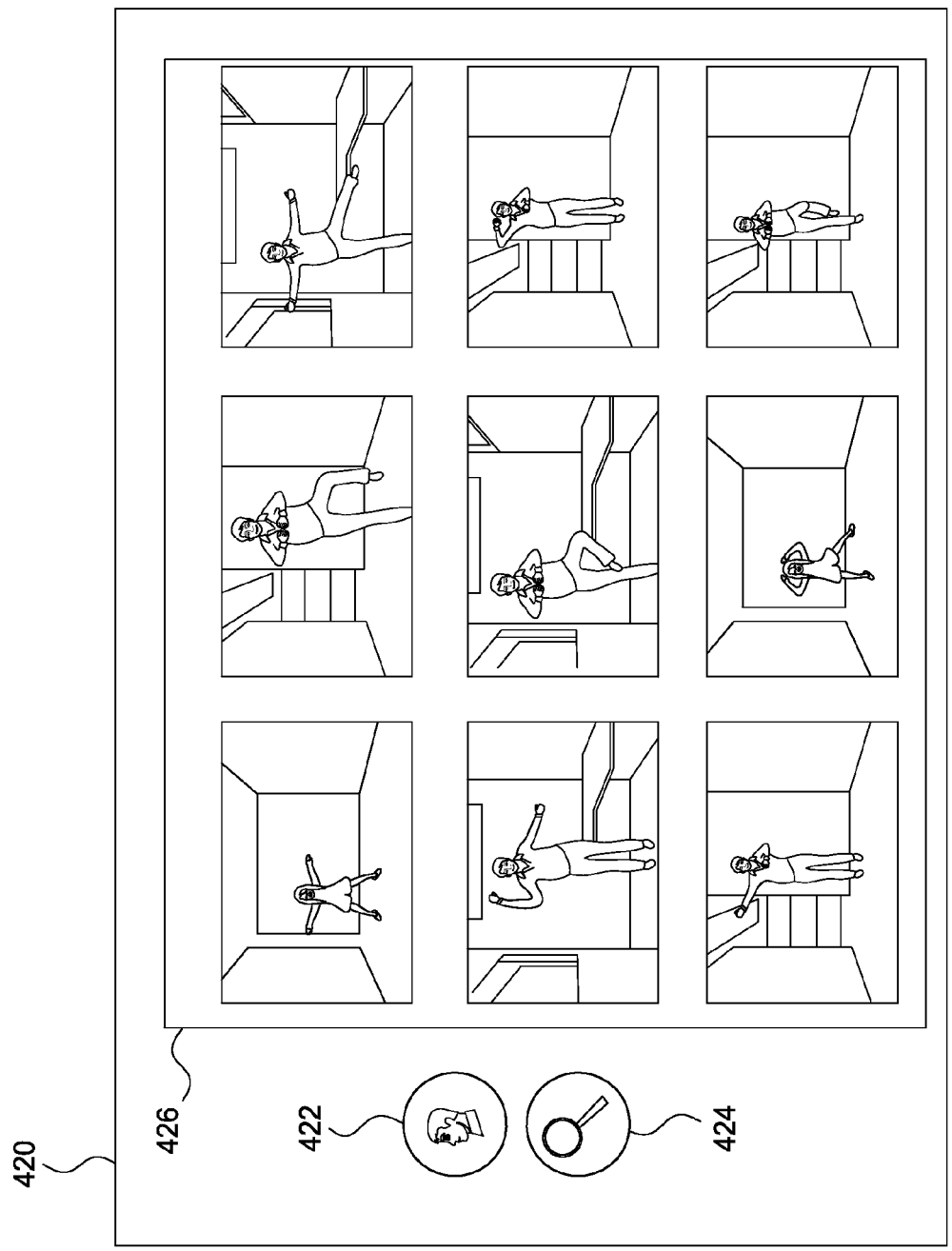
FIG. 4B illustrates a movement gallery user-interface screen, according to one embodiment of the present invention.

FIG. 4B illustrates a movement gallery user-interface screen 420, according to one embodiment of the present invention. As shown, the movement gallery user-interface screen 420 includes a user profile button 422, a search button 424, and a gallery of movements 426 corresponding to sorted search results.

The user profile button 422 allows the user 350 to select a user profile from a set of user profiles. The user profile button 422 allows multiple trainees to save and later restore personalized progress and score data for any movements previously selected for training.

The search button 424 allows the user 350 to search for movements by example. When the user 350 selects the search button 424, an instruction box appears (not shown) that instructs the user 350 to perform a representative movement or hold a representative posture of the desired movement.

The user 350 may query the movement database 242 based on holding a static posture. A search screen (not shown) is presented that instructs the user 350 to hold a representative posture of the desired movement. After the user assumes the posture and stays still for a specific duration, such as three seconds, the movement training system 200 captures the posture via the motion tracking module 225 and searches the movement database 242 for movements that best match the posture held by the user 350. The motion tracking unit 320 provides three-dimensional (3D) motion capture tracking of one or more joint positions of a user, such as twenty joints. The motion tracking unit 320 provides updated joint positions at multiple times per second, such as thirty times per second. The tracked joint positions are typically coarse positioning associated with large body parts, such as the hands, arms, torso, legs and head, but do not typically include fine positioning, such as joint positions related to fingers and toes. The movement training system 200 creates a skeletal representation from the captured posture.

The movement training system 200 calculates a similarity score between the current posture and each posture in the movement database 242 by comparing the skeletal representation with corresponding skeletal representations of the movements in the movement database 242. A high similarity score indicates that two skeletal representations are more similar, while a low similarity score indicates that two skeletal representations are less similar.

Before computing the similarity score, the movement training system 200 scales and translates the captured skeleton to match the skeletal representation in the movement database 242. This operation enables comparing a skeletal representation of a child with a skeletal representation of an adult, for example. Spatial alignment is performed by aligning the hips of the captured skeletal representation with the hips of the skeletal representation of a movement in the movement database 242. The movement training system 200 scales the captured skeletal representation by dynamically resizing each bone in the captured skeletal representation to match the size of the corresponding bone in the skeletal representation of a movement in the movement database 242. Scaling is performed hierarchically from the hips to propagate changes throughout the skeletal representation, because simple uniform scaling may not accommodate users with proportionally different limb lengths. As a result, skeletal representations may be compared even when the user 350 has a significantly different age, height or weight from the author of the stored movement.

The movement training system 200 computes the similarity score based on the joint with the maximum difference between the skeletal representations, as measured by Euclidean distance. In one embodiment, all joint distances may be computed, and the average or median value may be used as the similarity score. In an alternative embodiment, a subset of the joints may be considered when computing the similarity score. The subset of joints may be those joints which are relevant to the current posture. The movement training system 200 displays those movements with higher similarity scores in the gallery of movements 426.

Alternatively, the user 350 may query the movement database 242 based on performing a dynamic movement. For this form of query, the user 350 begins a movement capture by remaining still for a duration of time, such as three seconds. The user 350 then performs a movement. To complete the recording, the user again remains still for a duration of time, such as three seconds. The movement training system 200 computes a similarity score, as described above, between the captured movement and each movement in the movement database 242.

In one embodiment, the movement training system 200 creates one or more feature vectors based on the captured movements and the stored movement. The movement training system 200 then computes the similarity of the feature vectors. Various possible features may be used to create the feature vectors, including, without limitation, average joint velocity, individual joint velocities, starting and final joint positions, and starting and final bone orientations. In another embodiment, the movement training system 200. The second implementation is to compares the movements by comparing the skeletal representations at each frame of the two movements.

The movement training system 200 may compare the entire captured movement with the entire stored movement. Alternatively, the user 350 may capture a subset of a particular movement training system 200 to compare against the movements in the movement database 242. The movement training system 200 may perform the search on all subsets of the movements in the movement database 242. Subset similarity scores may be based on movement subsets demarked by major inflection points in the movement.

Once the user 350 performs the movement or holds the posture, the user 350 remains still for a period of time until the movement training system 200 identifies that the movement or posture has been captured. The movement training system 200 searches the movement database 242 for those movements that match most closely with the movement or posture performed by the user 350. The search results are sorted in order of likelihood of match, from the most likely movement to the least likely movement.

The gallery of movements 426 illustrates thumbnail images of the most likely movements, as indicated by the sorted search results. The user 350 may select one of the movements in the gallery of movements 426, or may scan to other sets of thumbnail images until the desired movement is found. The user 350 then selects the desired movement as the target movement and begins training for the target movement.

Training progresses as a series of stages, phases or modules, where the user 350 is scored at each module based on the user's performance as measured by the similarity between the movement performed by the user 350 and the target movement. When computing the score for the user 350, the movement training system 200 scales the skeletal representation of the user 350 to match the skeletal representation of the target movement and computes a similarity score, as described above. Each keyframe in the target movement is scored based on the joint with the maximum error, as measured by Euclidean distance. The similarity score may be based on a subset of joints specified as important joints by the author of the movement. The movement training system 200 may allow a timing margin of 0.5 seconds, for example, before and after the target keyframe when computing the similarity score, to allow for small timing errors made by the user 350. If the author of the target movement specified that timing is important, then this window may be decreased to 0.25 seconds, for example. The maximal Euclidean distance may be mapped to a score using a linear mapping, where an error of 0 meters corresponding to a score of 10 and an error of 0.15 m corresponding to a score of 7.5. If the author of the target movement specifies precision as an important parameter, then the mapping may be modified such that an error 0.10 meter corresponds to a score of 7.5. A score of 7.5 may correspond to the minimum score needed for the user 350 to progress to the next module.

FIG. 4C illustrates a training module selection user-interface screen 430, according to one embodiment of the present invention. As shown, the training module selection user-interface screen 430 includes a movement gallery navigation button 426, a demonstration selection button 428, a posture guide selection button 432, a movement guide selection button 434, a mirror selection button 436, and an "on your own" selection button 438.

The movement gallery navigation button 426 allows the user to navigate to the movement gallery user-interface screen 420 to select a different target movement for training. The demonstration selection button 428, posture guide selection button 432, movement guide selection button 434, mirror selection button 436, and on your own button 438 allow the user to navigate to the demonstration, posture guide, movement guide, mirror, and on your own modules, respectively. The check mark on the demonstration selection button 428 and posture guide selection button 432 indicates that the modules are unlocked for the target movement, and the user is permitted to navigate to the corresponding modules. The lock on the movement guide selection button 434, mirror selection button 436, and on your own selection button 438 indicates that the modules are locked for the target movement, and the user is not yet permitted to navigate to the corresponding modules.

The demonstration, posture guide, movement guide, mirror, and on your own modules progressively introduce the target movement to the user 350, with gradual reduction in reliance on guidance and feedback. Each module presents the user 350 with a different context in which to perform the target movement, as further described below. In one embodiment, certain modules may be repeated multiple times automatically, allowing users to practice without being interrupted. For example, the posture guide module could repeat twice, and the movement guide, mirror and on your own module could repeat five times.

Figure 4D:
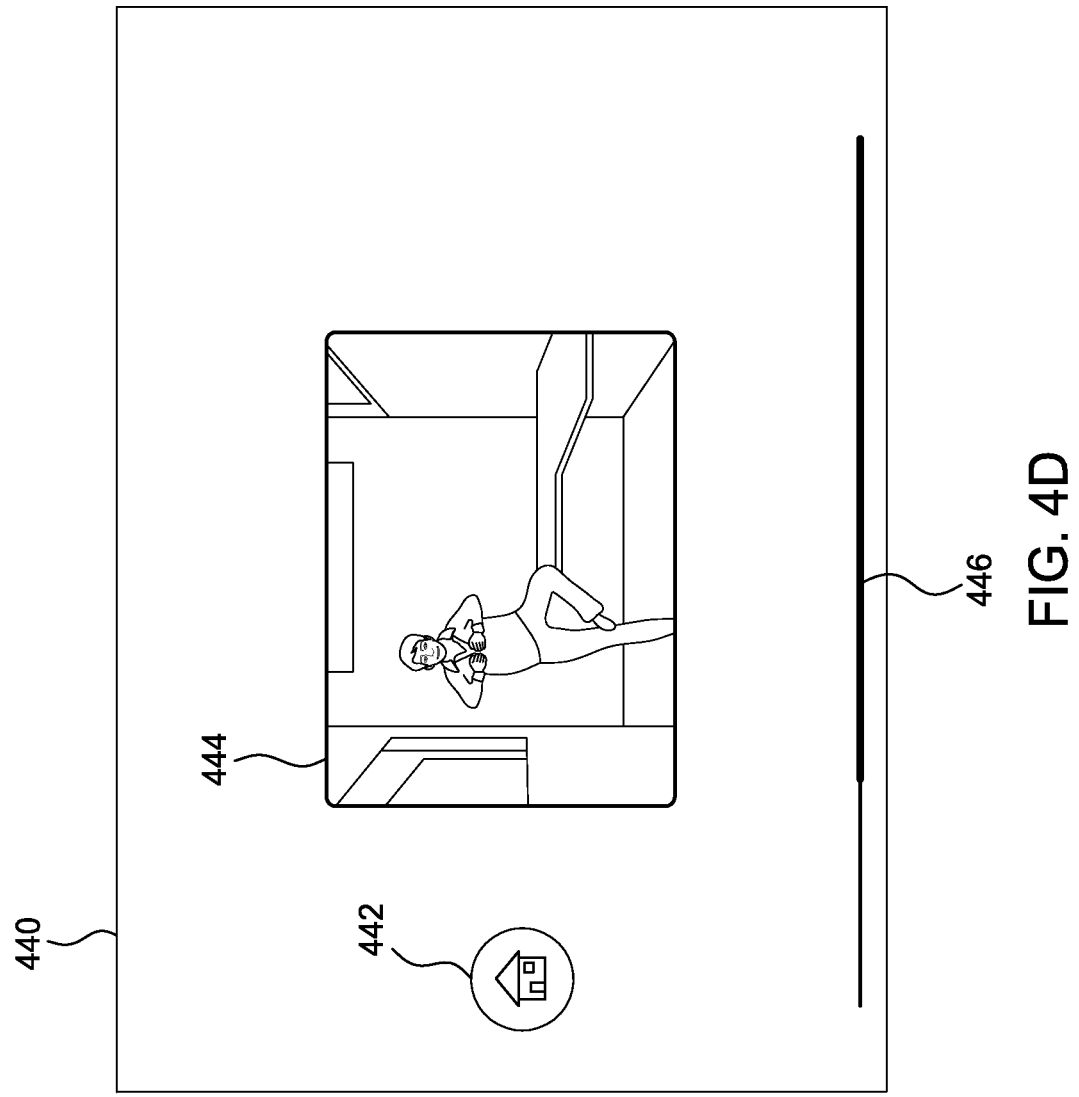
FIG. 4D illustrates a demonstration user-interface screen, according to one embodiment of the present invention.

FIG. 4D illustrates a demonstration user-interface screen 440, according to one embodiment of the present invention. As shown, the demonstration user-interface screen 440 includes a training module navigation button 442, a demonstration video window 444, and a progress bar 446.

The training module navigation button 442 allows the user to navigate to the training module selection user-interface screen 430 to select a different training module for the current target movement.

The demonstration video window 444 provides a display of the target movement. The movement training system 200 adjusts the dimmable light source 340 in the movement training environment 300 so that the user 350 sees only the projected image and not the reflected image. The movement training system 200 plays a recorded video of the target movement for the user 350. In some embodiments, the movement training system 200 may also play an audio signal along with the video to provide synchronization signaling related to the target movement. For example, the audio signal could be a pre-recorded voice that says "And, one, two, three, . . . " in time with specified keyframes. This audio signal may be present in all training modules except for the on your own module.

The progress bar 446 indicates a position along a timeline corresponding to the target movement.

Figure 4E:
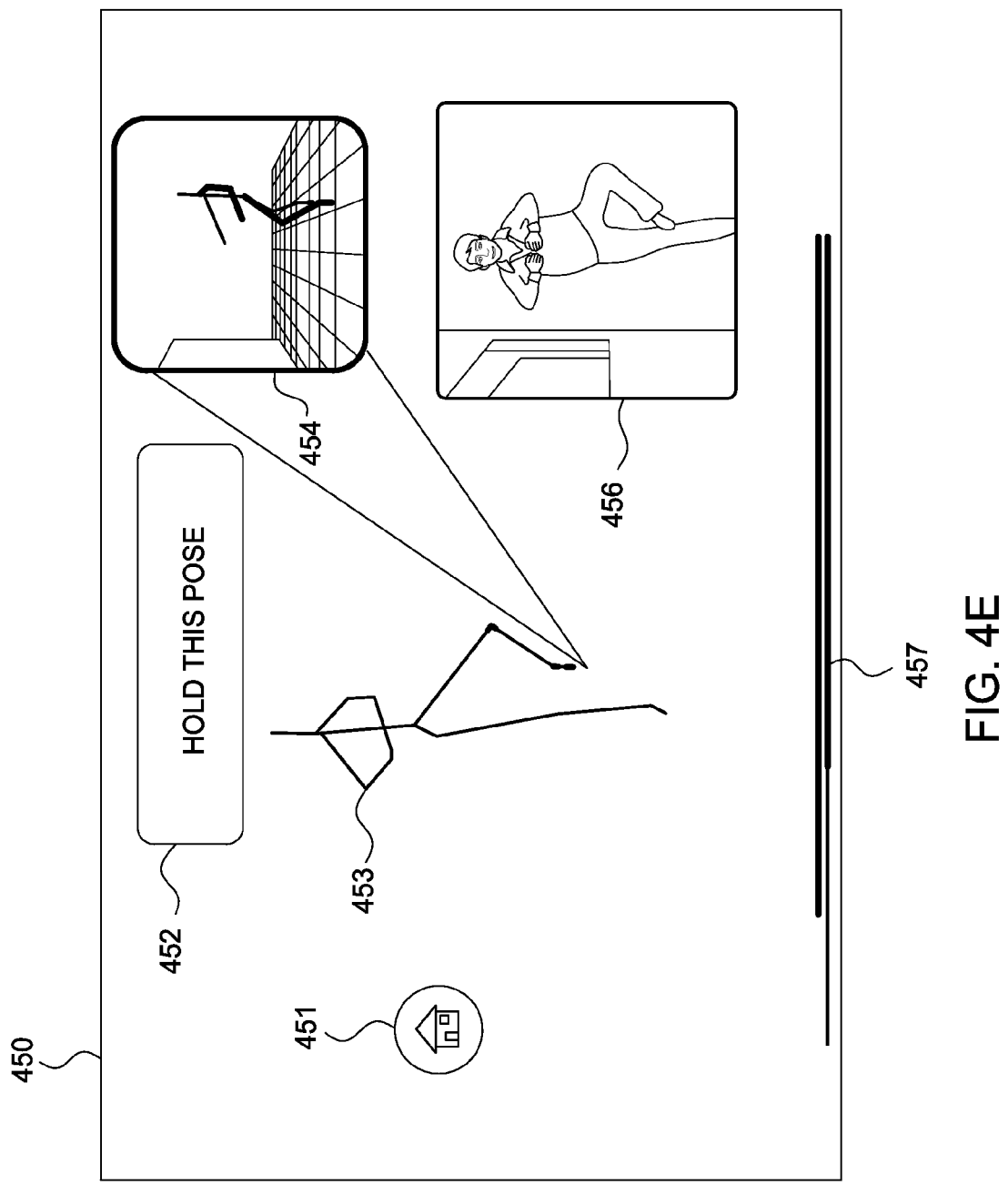
FIG. 4E illustrates a posture guide user-interface screen, according to one embodiment of the present invention.

FIG. 4E illustrates a posture guide user-interface screen 450, according to one embodiment of the present invention. As shown, the posture guide user-interface screen 450 includes a training module navigation button 451, a dialog box 452, a trainer skeletal representation 453, a profile representation window 454, a video window 456, and a progress bar 457. The training module navigation button 451 video window 456, and progress bar 457 function substantially the same as described in conjunction with FIG. 4D, except as further described below.

The trainer skeletal representation 453 represents the current position of the skeletal representation of the target movement. The movement training system 200 simultaneously plays the target movement in the video window 456 and presents a profile skeletal representation of the target movement in the profile representation window 454. The movement training system 200 may automatically crop the video in the video window 456 based on the location of the trainer within the video to preserve on-screen space. The movement training system 200 adjusts the dimmable light source 340 in the movement training environment 300 so that the user 350 sees both the projected image and the reflected image. As the user 350 performs the target movement, the movement training system 200 tracks the user 350 and dynamically updates the user skeletal representation 453. The trainer skeletal representation 453 is aligned to position of the user 350 for each frame of the movement. The user 350 is instructed to match his or her reflection in the augmented reality mirror 310 with the trainer skeletal representation 453. Errors in positioning may be shown as red circles overlaid on the joints of the trainer skeletal representation 453 or the user 350, where the circle radius is proportional to the amount of joint error. Error in a depth position may be shown on the profile representation window 454. In such cases, the profile representation window 454 displays a side view of the position of the user 350 overlaid with a side view of the target movement. In some embodiments, the profile representation window 454 may be displayed only when an error is detected in the depth dimension.

The movement training system 200 pauses the video and profile representation at each keyframe and presents a "Hold This Pose" message in the dialog box 452. The system remains paused until the user 350 holds the pose in a stable position for a duration of time, such as one second, or until a particular amount of time has elapsed, such as five seconds. These durations may be adjusted if stability is specified as a key parameter for the target movement.

The progress bar 457 is split into two portions, where one portion indicates a position along a timeline corresponding to the target movement. During a keyframe pause, the second portion indicates the amount of time the user 350 has held the current posture in a stable position.

Figure 4F:
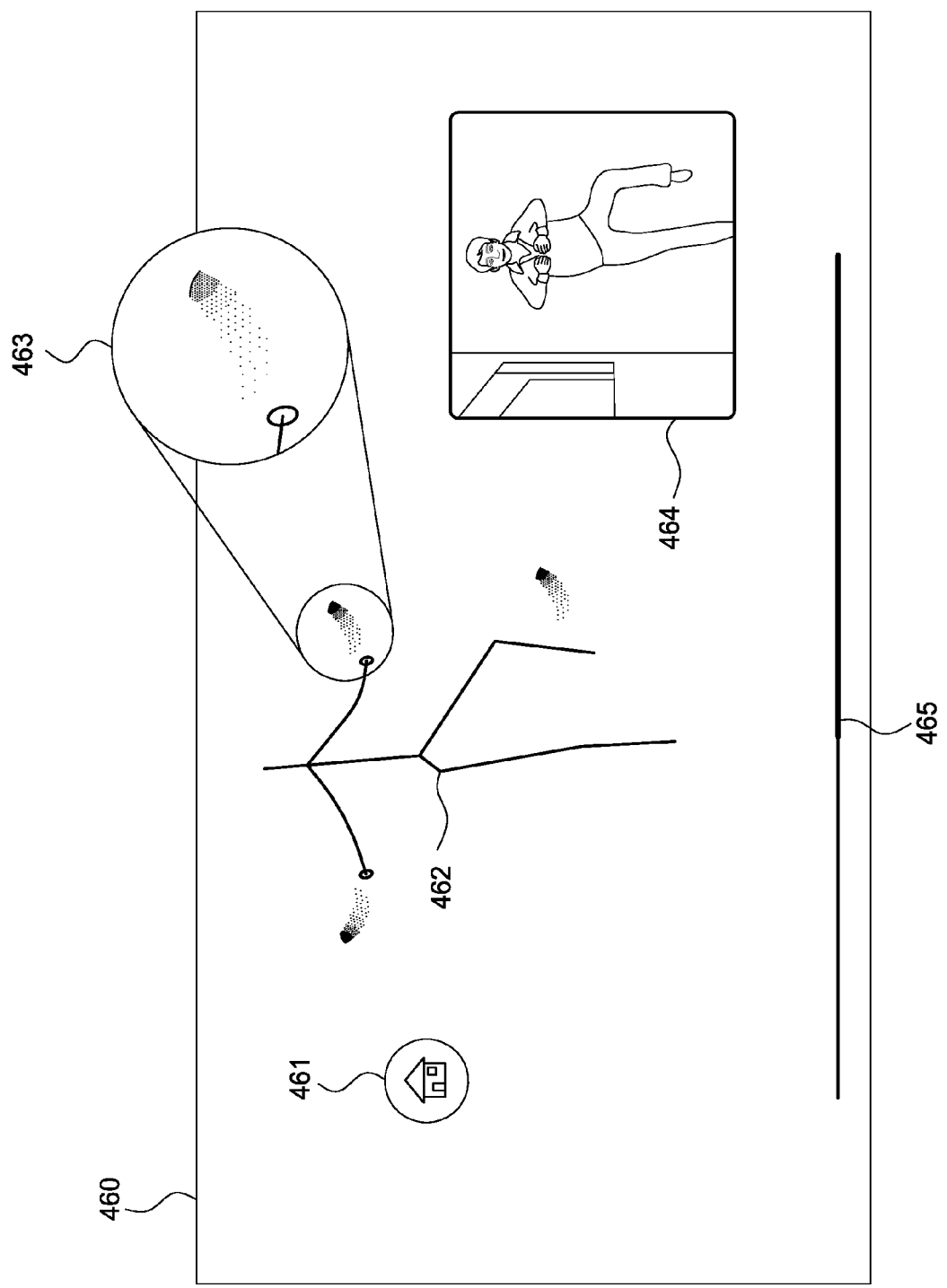
FIG. 4F illustrates a movement guide user-interface screen, according to one embodiment of the present invention.

FIG. 4F illustrates a movement guide user-interface screen 460, according to one embodiment of the present invention. As shown, the movement guide user-interface screen 460 includes a training module navigation button 461, a trainer skeletal representation 462, movement cues 463, a video window 464, and a progress bar 465. The training module navigation button 461, trainer skeletal representation 462, video window 464, and progress bar 465 function substantially the same as described in conjunction with FIGS. 4D-4E, except as further described below.

The movement training system 200 adjusts the dimmable light source 340 in the movement training environment 300 so that the user 350 sees both the projected image and the reflected image. The movement training system 200 causes a trainer skeletal representation 462 to be displayed along with a corresponding video window 464, as in the posture guide module. However, the trainer skeletal representation 462 moves in real-time without pausing on the keyframes. In addition, the trainer skeletal representation 462 is aligned relative to the starting location of the user 350 on each repetition of the movement guide module, thus guiding the user 350 to maintain alignment with the trainer skeletal representation 462

The movement cues 463 provide additional guidance as the user 350 performs the movement. The movement cues 463 take the form of "cue ribbons" that indicate 3D trajectories related to the direction of movement. As shown, the movement cues 463 display the trajectory of the hands and feet for a duration of time, such as 300 ms, ahead of the current frame. In some embodiments, the movement cues 463 are more transparent for near term movement, becoming more opaque for more distant times in the future. In some embodiments, the movement cues 463 are displayed only when corresponding joints of the user are expected to surpass a threshold speed, such as 75 cm/s, within the next 300 ms. Employing such a threshold may reduce visual complexity by displaying movement cues 463 only when rapid motion of one or more joints is expected. If smoothness is indicated as an important parameter for the current movement, the movement cues may display the trajectory of the hands and feet for a longer duration of time ahead of the current frame, such as 500 ms.

In the mirror module (not explicitly shown) the user 350 performs the target movement by watching the reflection in the augmented reality mirror 310 without any projected visual cues to guide the movements. The movement training system 200 adjusts the dimmable light source 340 in the movement training environment 300 and causes the projector 330 to project a dark image so that the user 350 sees only the reflected image and not the projected image. In some embodiments, audio cues may be present as a timing aid, as described above.

In the on your own module (not explicitly shown) the user 350 performs the target movement without any aid from projected visual cues or from the reflection. The movement training system 200 adjusts the dimmable light source 340 in the movement training environment 300 and causes the projector 330 to project a bright image so that the user 350 sees neither the reflected image nor the projected image. In some embodiments, audio cues may be present as a timing aid, as described above. Alternatively, the audio cues may include only the word "and" to indicated the beginning the movement, without counting out the beats of the movement.

Figure 4G:
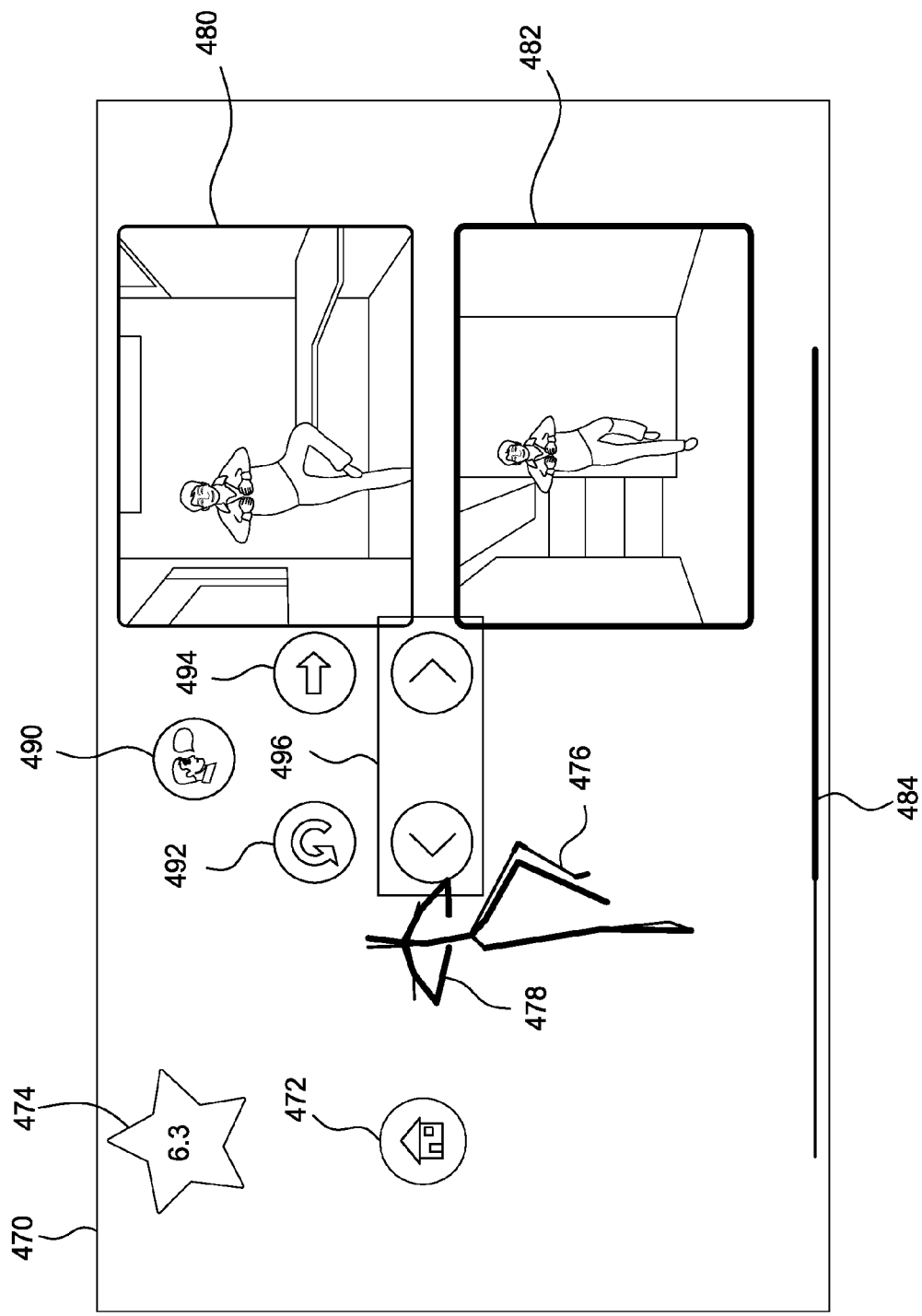
FIG. 4G illustrates a post-module feedback user-interface screen, according to one embodiment of the present invention.
Figure 5A:
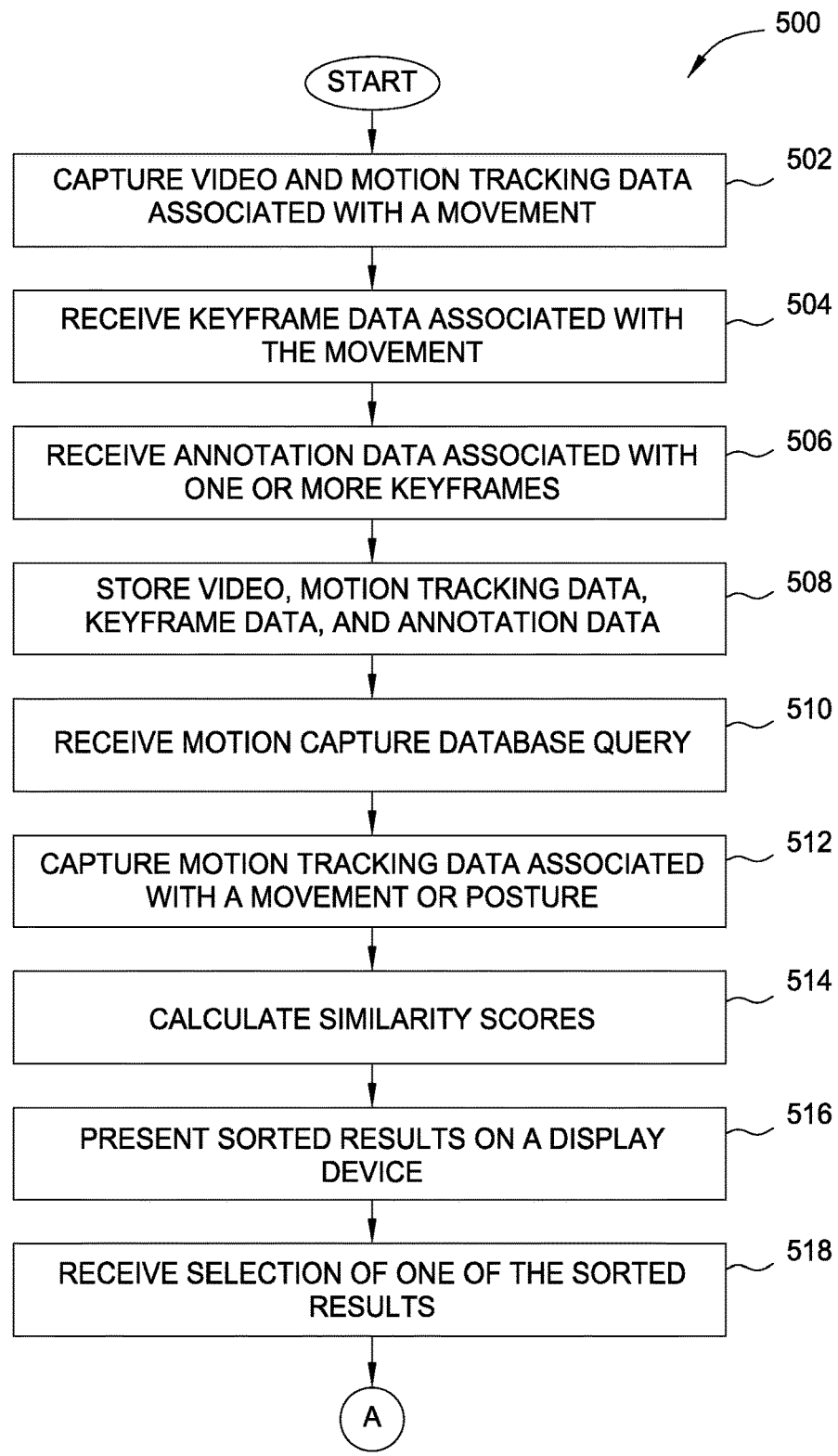
FIGS. 5A-5F set forth a flow diagram of method steps for controlling a movement training environment, according to one embodiment of the present invention.
Figure 5B:
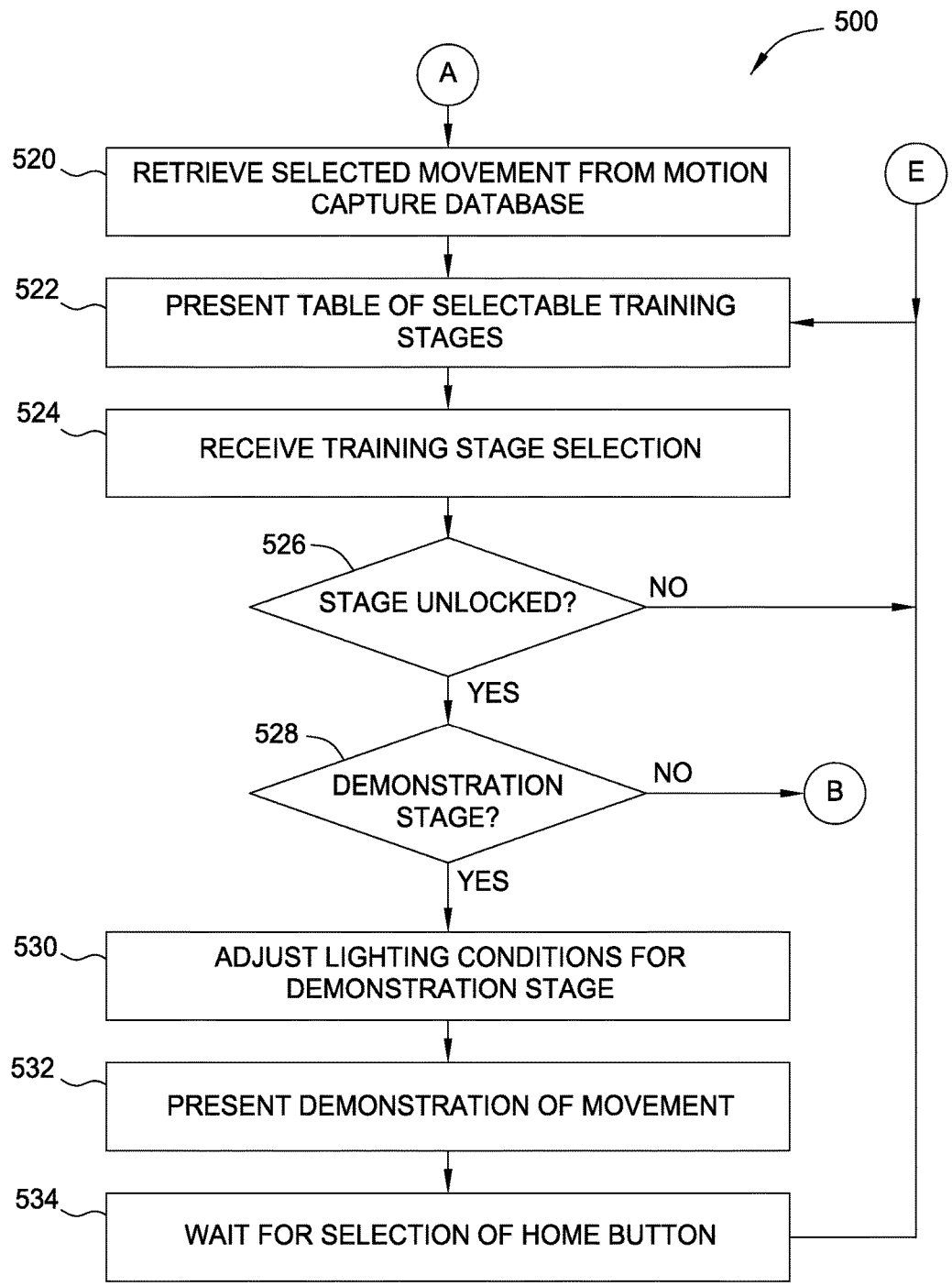
Figure 5C:
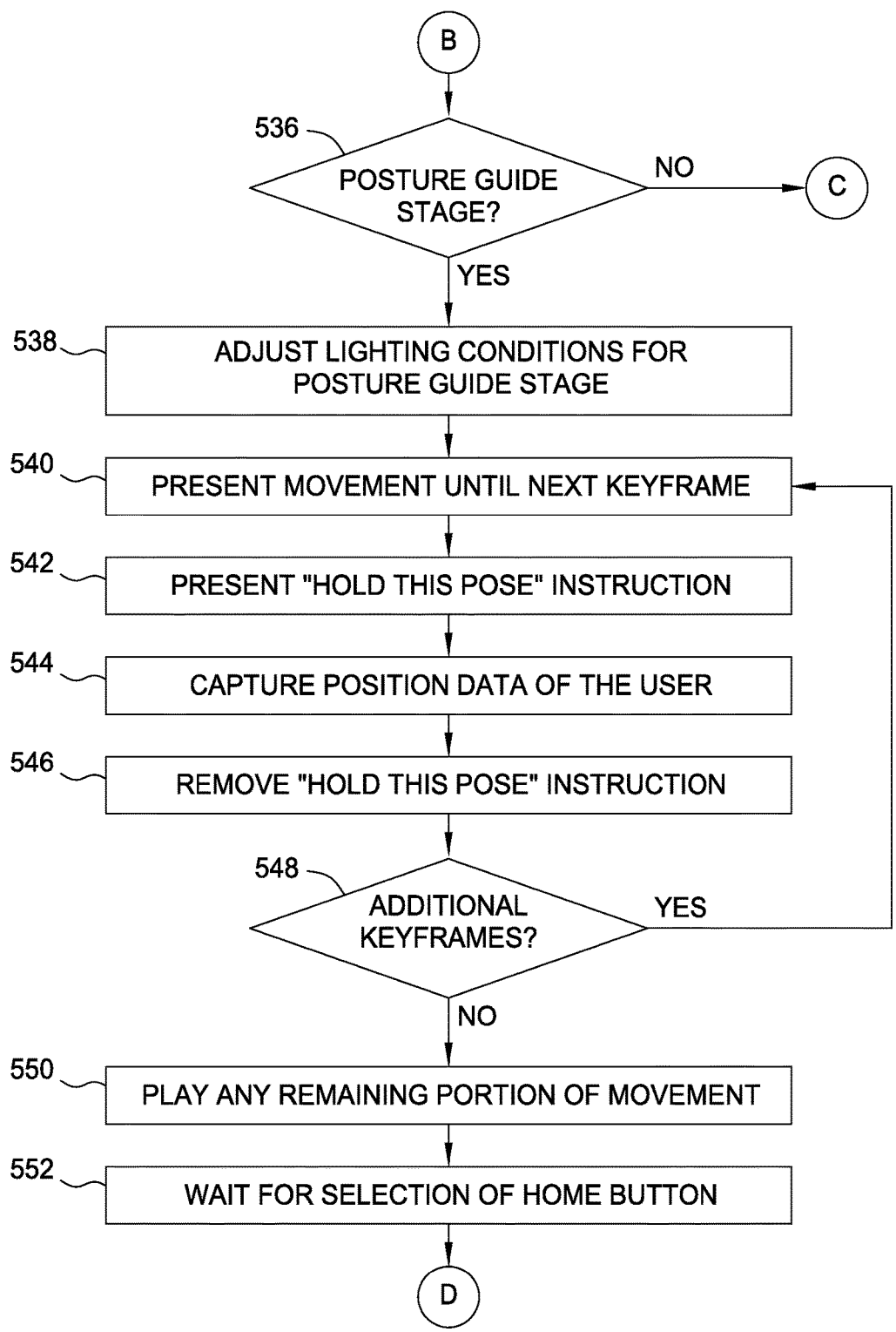
Figure 5D:
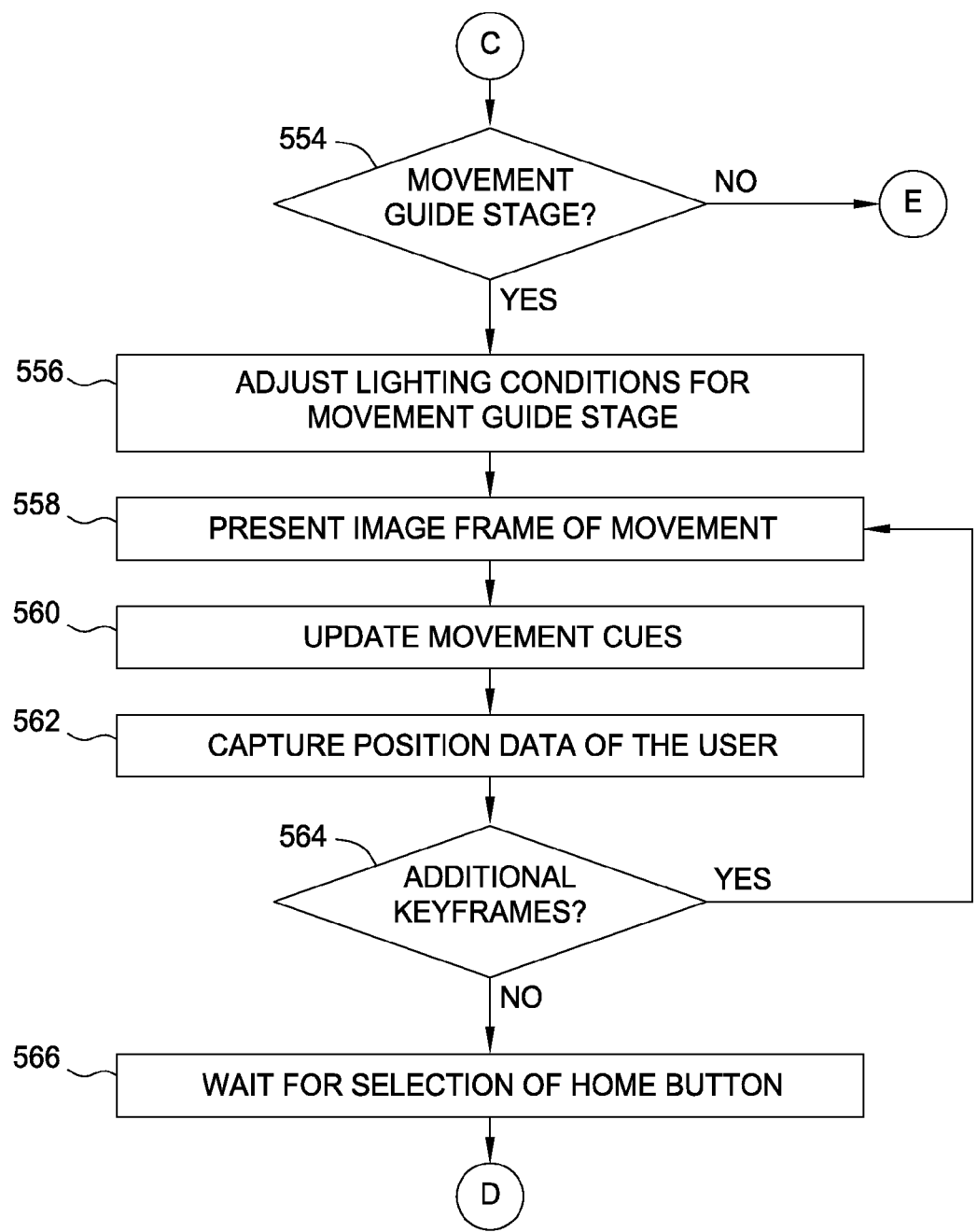
Figure 5E:
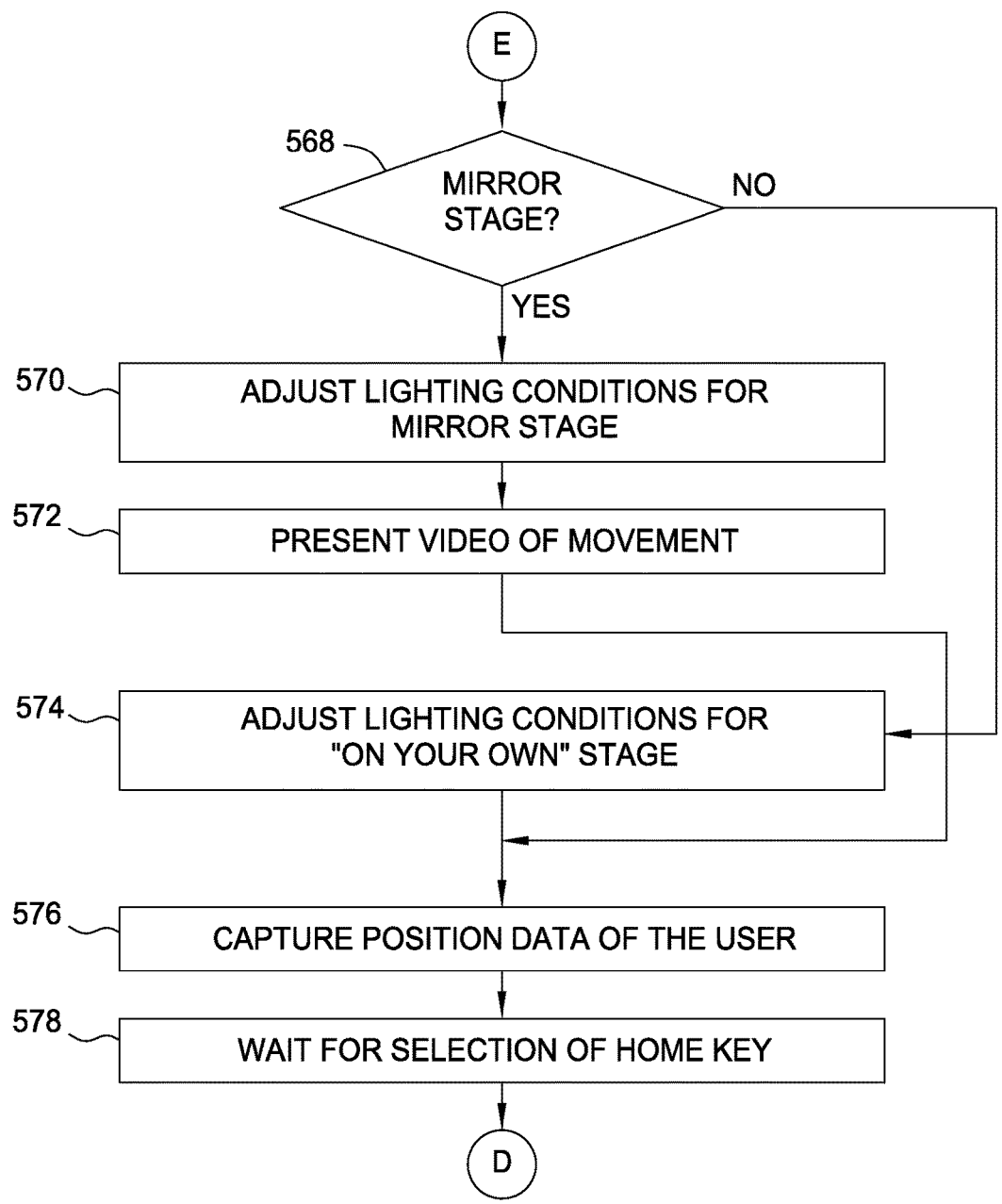
Figure 5F:
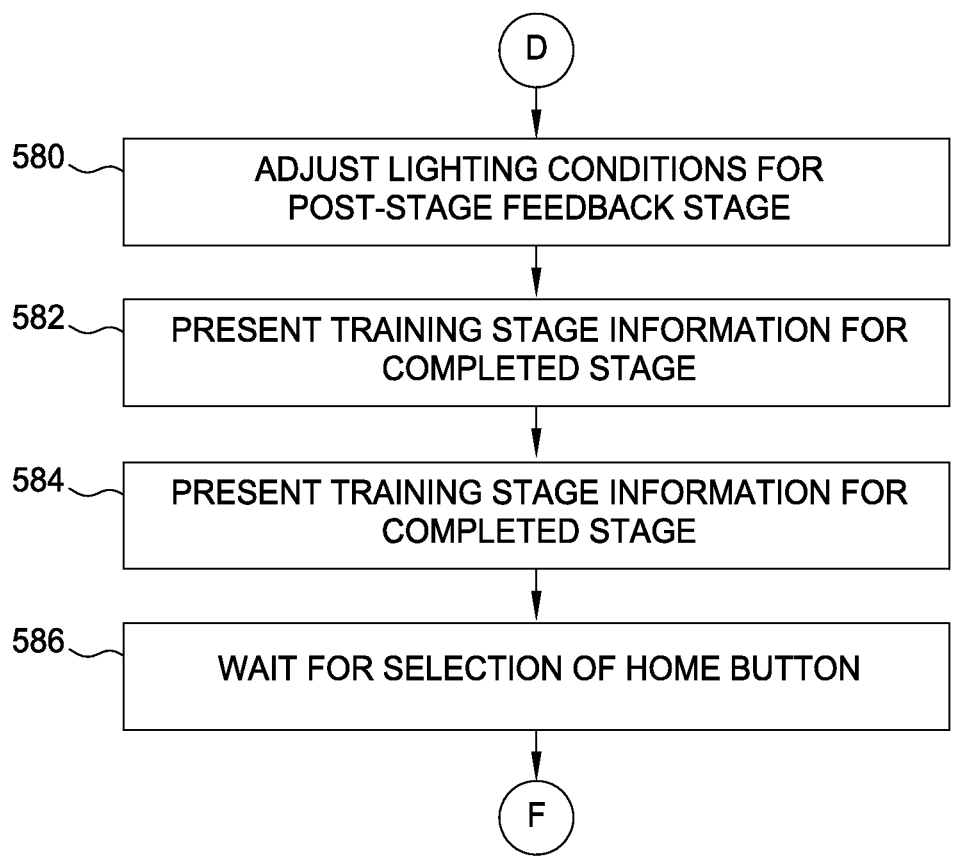

FIG. 4G illustrates a post-module feedback user-interface screen 470, according to one embodiment of the present invention. As shown the post-module feedback user-interface screen 470 includes a training module navigation button 472, a score display 474, a trainer skeletal representation 476, a user skeletal representation 478, a trainer video window 480, a user video window 482, a progress bar 484, an annotation button 490, a repeat module button 492, a next module button 494, and keyframe navigation buttons 496.

The training module navigation button 472, trainer skeletal representation 476, trainer video window 480, and progress bar 484 function substantially the same as described in conjunction with FIGS. 4D-4F, except as further described below.

The user 350 may view performance for the target movement with the post-module feedback user-interface screen 470. The post-module feedback user-interface screen 470 is displayed after the user 350 completes each of the training modules, except the demonstration module. The post-module feedback user-interface screen 470 includes displays regarding how well the user 350 performed during the previous module. The movement training system 200 adjusts the dimmable light source 340 in the movement training environment 300 and causes the projector 330 to project a grey image so that the user 350 sees the projected image and also sees the reflected image, enabling the user 350 to see his or her reflection and select on screen user-interface elements.

The score display 474 presents the score achieved by the user for the current keyframe of the target movement.

The trainer skeletal representation 476 and the user skeletal representation 478 are overlaid so that the user 350 may compare his or her movement with the target movement. Circles or other suitable markers indicate relative joint position errors, as described in conjunction with FIG. 4E. While viewing the trainer skeletal representation 476 and the user skeletal representation 478, the user 350 may rotate the 3D view of the skeletal representations 476 and 478 by walking left or right in front of the augmented reality mirror 310 or by performing another suitable gesture.

Similarly, a trainer video window 480 shows video of the target movement video while the user video window 482 simultaneously shows video of the user 350 performing the target movement, enabling the user 350 to quickly assess his or her movements as compared with the target movement. The trainer video window 480 may present a static image taken from the recorded video for the target movement, while the user video window 482 presents an animated sequence of images, where each image represents one repetition of the movement from the completed module. Each representative user image may be displayed in sequence for a duration, such as 0.5 seconds, enabling the user 350 to detect variations among the repetitions of the posture or movement.

The annotation button 490 allows the user 350 to view a video, audio, or textual annotation associated with the current keyframe, if such an annotation is associated with the current keyframe.

The repeat module button 492 allows the user to repeat the recently completed module, while the next module button 494 allows the user 350 to advance to the next module.

The keyframe navigation buttons 496 allow the user 350 to navigate to previous and following keyframes, enabling the user 350 to view an average score for that keyframe, as well as the skeletal representations 476 and 478 and video windows 480 and 482 for the previous and following keyframes.

It will be appreciated that the system shown herein is illustrative and that variations and modifications are possible. For example, although the approaches set forth herein are described in the context of a system that Implements both the authoring of a movement by a first user and the use of the movement by a second user, the disclosed approaches could be implemented with two separate systems, one system that includes an authoring application program to enable a first user to record and author movement data and a second independent training system that includes an application program to enable a second user to access the movement data in order to learn how to reproduce the movement.

FIGS. 5A-5F set forth a flow diagram of method steps for controlling a movement training environment, according to one embodiment of the present invention. Although the method steps are described in conjunction with the systems of FIGS. 1-4G, persons of ordinary skill in the art will understand that any system configured to perform the method steps, in any order, is within the scope of the present invention.

As shown, a method 500 begins at step 502, where the video capture module 220 captures video associated with a movement performed by a first user. Simultaneously, the motion tracking module 230 captures motion tracking data associated with the movement performed by the first user. The first user may be a teacher or trainer who initiates the data capture by, for example, selecting a record function on a GUI. At step 504, the movement training application 210 receives keyframe data associated with the movement, where the keyframe data corresponds to one or more keyframes identified by the first user. Each keyframe represents an image frame from the captured movement that the first user identifies as particularly important for the movement. At step 506, the movement training application 210 receives annotation data associated with one or more keyframes, where annotation data includes auxiliary information provided by the first user for the corresponding keyframe. The auxiliary information, includes, without limitation, text, audio, or video information considered by the first user to be helpful for the pose displayed at the corresponding keyframe. At step 508, the movement training application 210 stores the movement in the movement database 242, where the movement includes, without limitation, the video, motion tracking data, keyframe data, and annotation data.

At step 510, the movement training application 210 receives a movement database query from a second user. The second user may be a student or trainee who initiates the database query to select a previously captured motion to learn. At step 512, the motion tracking module 230 captures motion tracking data associated with a movement performed by the second user or a posture held by the second user for a duration of time. At step 514, the movement training application 210 calculates similarity scores, where each similarity score measures the level of similarity between the captured movement or posture and a different movement or posture from the movement database 242. At step 516, the projector 250 presents sorted results on a display device, where the results are sorted based on the similarity scores. At step 518, the movement training application 210 receives a selection by the second user of one of the sorted results. At step 520, the movement training application 210 retrieves the selected result from the movement database, where the selected result corresponds to the movement that the second user wants to learn.

At step 522, the projector 250 presents a table of selectable training modules for the movement. At step 524, the movement training application 210 receives a training module selection from the second user. At step 526, the movement training application 210 determines whether the selected training module is unlocked. For example, a training module may be unlocked after the second user has completed the prior training modules for the movement. If the selected training module is not unlocked, then the method 500 proceeds to step 522, described above.

If, however, the selected training module is unlocked, then the method 500 proceeds to step 528, where the movement training application 210 determines whether the selected training module is the demonstration module. If the selected training module is the demonstration module, then the method 500 proceeds to step 530, where the movement training application 210 controls the dimmable light source 340 to adjust the lighting conditions for the demonstration module, such that the second user sees only the projected image on the augmented reality mirror 310 and not the reflected image. At step 532, the projector 250 presents a demonstration of the movement by playing the entire movement. At step 534, the movement training application 210 waits for the second user to select the home button on the GUI. After the second user the selects the home button, the method 500 then proceeds to step 522, described above.

Returning to step 528, if the selected training module is not the demonstration module, then the method 500 proceeds to step 536, where the movement training application 210 determines whether the selected training module is the posture guide module. If the selected training module is the posture guide module, then the method 500 proceeds to step 538, where the movement training application 210 controls the dimmable light source 340 to adjust the lighting conditions for the posture guide module, such that the second user sees both the projected image and the reflected image on the augmented reality mirror 310. At step 540, the projector 250 presents the movement until the next keyframe is reached. At step 542, the projector 250 presents a "hold this pose" instruction to the second user. At step 544, the motion tracking module 230 captures position data of the second user. At step 546, the projector 250 removes the "hold this pose" instruction after a fixed duration or, alternatively, after the second user holds the pose corresponding to the current keyframe for a minimum period of time. At step 548, the movement training application 210 determines whether additional keyframes remain for the movement. If additional keyframes remain, then the method 500 proceeds to step 540, described above. If, however, no additional keyframes remain, then the method 500 proceeds to step 550, where the projector 240 presents any remaining portion of the movement. At step 552, the movement training application 210 waits for the second user to select the home button on the GUI.

After the second user selects the home button, the method 500 then proceeds to step 580, where the movement training application 210 controls the dimmable light source 340 to adjust the lighting conditions for the post-module feedback module, such that the second user sees both the projected image and the reflected image on the augmented reality mirror 310. At step 582, the projector 250 presents training module information regarding the most recently completed module to the second user, including, without limitation, the second user's current performance score for the movement, an overlay of the movement as performed by the first user with the movement as performed by the second user, video of the first user performing the movement, video of the second user performing the movement, and navigation buttons. At step 584, the movement training application 210 interacts with the second user as the second user instructs the movement training system 200 to repeat the most recently completed module, advance to the next module, navigate to prior or next keyframes, access annotation data for a particular keyframe. At step 586, the movement training application 210 waits for the second user to select the home button on the GUI. After the second user the selects the home button, the method 500 then proceeds to step 522, described above.

Returning to step 536, if the selected training module is not the posture guide module, then the method 500 proceeds to step 554, where the movement training application 210 determines whether the selected training module is the movement guide module. If the selected training module is the movement guide module, then the method 500 proceeds to step 556, where the movement training application 210 controls the dimmable light source 340 to adjust the lighting conditions for the movement guide module, such that the second user sees both the projected image and the reflected image on the augmented reality mirror 310. At step 558, the projector 250 presents an image frame from the movement. At step 560, the movement training application 210 updates movement cues that are then presented by the projector 250 to identify upcoming changes to the movement, thereby assisting the second user in properly performing the movement. At step 562, the motion tracking module 230 captures position data of the second user. At step 564, the movement training application 210 determines whether additional image frames remain for the movement. If additional image frames remain, then the method 500 proceeds to step 558, described above. If, however, no additional keyframes remain, then the method 500 proceeds to step 566, where the movement training application 210 waits for the second user to select the home button on the GUI. After the second user selects the home button, the method 500 then proceeds to step 580, described above.

Returning to step 554, if the selected training module is not the movement guide module, then the method 500 proceeds to step 568, where the movement training application 210 determines whether the selected training module is the mirror module. If the selected training module is the mirror module, then the method 500 proceeds to step 570, where the movement training application 210 controls the dimmable light source 340 to adjust the lighting conditions for the mirror module, such that the second user sees only the projected image on the augmented reality mirror 310 and not the reflected image. At step 572, the projector 250 presents the movement. At step 576, the motion tracking module 230 captures position data of the second user as the second user performs the movement. At step 578, the movement training application 210 waits for the second user to select the home button on the GUI. After the second user selects the home button, the method 500 then proceeds to step 580, described above.

Returning to step 568, if the selected training module is not the mirror module, then the method 500 proceeds to step 574, where the movement training application 210 controls the dimmable light source 340 adjusts the lighting conditions for the "on your own" module, such that the second user sees only the reflected image on the augmented reality mirror 310 and not the projected image. The method 500 then proceeds to step 576, described above.

In sum, a movement training system interfaces with a movement training environment to enable trainees, or other users, to learn new movements for a variety of applications, such as dance or sports. The movement training environment includes an augmented reality mirror that allows users to view images from a projector, images reflected off the augmented reality mirror, or both projected and reflected images. An author creates one or more movements, where a movement includes video and motion capture data of a physical movement along with video, audio, or textual annotations associated with keyframes in the movement. The authored movements are stored in a movement database.

A trainee selects a movement by holding a pose or performing the movement. The movement training system captures the user's pose or movement and then compares the user's pose or movement with the movements stored in the database. The movement training system presents the most likely movements based on the comparison, and the trainee selects the desired movement. The trainee then progresses through a series of modules where the user watches a demonstration of the movement, learns key poses in the movement, learns the entire movement, and then performs the movement with and without the aid of a reflection. After completing certain modules, the trainee observes an evaluation of his or her performance of the movement as compared with the authored movement.

One advantage of the disclosed techniques is that users learn new movements interactively without the need for live instruction and without the limitations of other remote training approaches. Users may quickly navigate to different movements, different modules of a particular movement, and different keyframes of the movement to focus training where most needed. As a result, trainees may increase proficiency more quickly than with other remote movement learning techniques.

Various embodiments of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

The invention has been described above with reference to specific embodiments and numerous specific details are set forth to provide a more thorough understanding of the invention. Persons skilled in the art, however, will understand that various modifications and changes may be made thereto without departing from the broader spirit and scope of the invention. The foregoing description and drawings are, accordingly, to be regarded in an illustrative rather than a restrictive sense. In view of the foregoing, the scope of the present invention is determined by the claims that follow.

What is claimed is:

1. A method implemented via a computer for controlling a movement training environment, the method comprising:
   retrieving a movement object from a plurality of movement objects stored in a memory, wherein the movement object comprises a first keyframe and first annotation data that includes auxiliary information corresponding to the first keyframe;
   attaining first motion capture data associated with a first user performing a movement based on the movement object;
   generating a first articulable representation based on the first motion capture data;
   comparing at least one first joint position related to the first articulable representation with at least one second joint position related to a second articulable representation associated with the movement object;
   calculating, via a processor, a first similarity score for the first keyframe based on a difference between the at least one first joint position and the at least one second joint position; and
   displaying the movement object, including the first annotation data, and the first similarity score on a display device.

2. The method of claim 1, further comprising:
   attaining second motion capture data associated with a second user performing the movement;
   generating the second articulable representation based on the second motion capture data;
   recording a video segment of the second user performing the movement; and
   storing the second articulable representation and the video segment in the movement object.

3. The method of claim 2, further comprising:
   receiving a selection of the first keyframe corresponding to a first point in time associated with the second articulable representation and a second point in time associated with the video segment;
   receiving annotation data related to the first keyframe; and
   storing the annotation data in the movement object.

4. The method of claim 1, further comprising:
   aligning the first articulable representation with the second articulable representation based on the at least one first joint position and the at least one second joint position to generate a composite articulable representation; and
   causing the composite articulable representation to be displayed on a display device.

5. The method of claim 1, further comprising:
   causing at least one of the first articulable representation and the second articulable representation to be projected onto a first surface of a half-silvered mirror; and
   transmitting a signal to a dimmable light source to adjust an ambient light in a room in which the half-silvered mirror is placed such that a second surface of the half-silvered mirror displays only the at least one of the first articulable representation and the second articulable representation.

6. The method of claim 1, further comprising:
   causing at least one of the first articulable representation and the second articulable representation to be projected onto a first surface of a half-silvered mirror; and
   transmitting a signal to a dimmable light source to adjust an ambient light in a room in which the half-silvered mirror is placed such that a second surface of the half-silvered mirror displays only a reflection of a portion of the room near the second surface.

7. The method of claim 1, further comprising:
   causing at least one of the first articulable representation and the second articulable representation to be projected onto a first surface of a half-silvered mirror; and
   transmitting a signal to a dimmable light source to adjust an ambient light in a room in which the half-silvered mirror is placed such that a second surface of the half-silvered mirror displays both the at least one of the first articulable representation and the second articulable representation and a reflection of a portion of the room near the second surface.

8. The method of claim 1, further comprising:
   comparing the at least one second joint position at a first point in time with the at least one second joint position at a second point in time;
   calculating a velocity of a joint associated with the at least one second joint position based on the at least one second joint position at the first point in time and the at least one second joint position at the second point in time;

determining that the velocity exceeds a threshold value;

generating a graphical element based on the at least one second joint position at the first point in time and the at least one second joint position at the second point in time.

9. The method of claim 1, further comprising:

attaining second motion capture data associated with the first user holding a posture;

generating a third articulable representation based on the second motion capture data;

for each movement object in the plurality of movement objects:

comparing at least one third joint position related to the third articulable representation with at least one joint position related to the articulable representation associated with the movement object, and calculating a similarity score based on a difference between the at least one third joint position and the at least one joint position related to the articulable representation; and selecting a subset of the plurality of movement objects that includes the first movement object based on the similarity scores.

10. The method of claim 1, further comprising:

attaining second motion capture data associated with the first user performing a movement;

generating a third articulable representation based on the second motion capture data;

for each movement object in the plurality of movement objects:

comparing at least one third joint position related to the third articulable representation with at least one joint position related to the articulable representation associated with the movement object, and calculating a similarity score based on a difference between the at least one third joint position and the at least one joint position related to the articulable representation; and selecting a subset of the plurality of movement objects that includes the first movement object based on the similarity scores.

11. A non-transitory computer-readable storage medium including instructions that, when executed by a processing unit, cause the processing unit perform an operation to control a movement training environment, the operation comprising:

retrieving a movement object from a plurality of movement objects stored in a memory, wherein the movement object comprises a first keyframe and first annotation data that includes auxiliary information corresponding to the first keyframe;

attaining first motion capture data associated with a first user performing a movement based on the movement object;

generating a first articulable representation based on the first motion capture data;

comparing at least one first joint position related to the first articulable representation with at least one second joint position related to a second articulable representation associated with the movement object;

calculating a first similarity score for the first keyframe based on a difference between the at least one first joint position and the at least one second joint position; and displaying the movement object, including the first annotation data, and the first similarity score on a display device.

12. The non-transitory computer-readable storage medium of claim 11, further comprising:

attaining second motion capture data associated with a second user performing the movement;

generating the second articulable representation based on the second motion capture data;

recording a video segment of the second user performing the movement; and storing the second articulable representation and the video segment in the movement object.

13. The non-transitory computer-readable storage medium of claim 12, further comprising:

receiving a selection of the first keyframe corresponding to a first point in time associated with the second articulable representation and a second point in time associated with the video segment;

receiving annotation data related to the first keyframe; and storing the annotation data in the movement object.

14. The non-transitory computer-readable storage medium of claim 11, further comprising:

aligning the first articulable representation with the second articulable representation based on the at least one first joint position and the at least one second joint position to generate a composite articulable representation; and causing the composite articulable representation to be displayed on a display device.

15. The non-transitory computer-readable storage medium of claim 11, further comprising:

causing at least one of the first articulable representation and the second articulable representation to be projected onto a first surface of a half-silvered mirror; and transmitting a signal to a dimmable light source to adjust an ambient light in a room in which the half-silvered mirror is placed such that a second surface of the half-silvered mirror displays only the at least one of the first articulable representation and the second articulable representation.

16. The non-transitory computer-readable storage medium of claim 11, further comprising:

causing at least one of the first articulable representation and the second articulable representation to be projected onto a first surface of a half-silvered mirror; and transmitting a signal to a dimmable light source to adjust an ambient light in a room in which the half-silvered mirror is placed such that a second surface of the half-silvered mirror displays only a reflection of a portion of the room near the second surface.

17. The non-transitory computer-readable storage medium of claim 11, further comprising:

causing at least one of the first articulable representation and the second articulable representation to be projected onto a first surface of a half-silvered mirror; and transmitting a signal to a dimmable light source to adjust an ambient light in a room in which the half-silvered mirror is placed such that a second surface of the half-silvered mirror displays both the at least one of the first articulable representation and the second articulable representation and a reflection of a portion of the room near the second surface.

18. The non-transitory computer-readable storage medium of claim 11, further comprising:

comparing the at least one second joint position at a first point in time with the at least one second joint position at a second point in time;

calculating a velocity of a joint associated with the at least one second joint position based on the at least one second joint position at the first point in time and the at least one second joint position at the second point in time;

determining that the velocity exceeds a threshold value;

generating a graphical element based on the at least one second joint position at the first point in time and the at least one second joint position at the second point in time.

19. The non-transitory computer-readable storage medium of claim 11, further comprising:

attaining second motion capture data associated with the first user holding a posture;

generating a third articulable representation based on the second motion capture data;

for each movement object in the plurality of movement objects:
  comparing at least one third joint position related to the third articulable representation with at least one joint position related to the articulable representation associated with the movement object, and
  calculating a similarity score based on a difference between the at least one third joint position and the at least one joint position related to the articulable representation; and selecting a subset of the plurality of movement objects that includes the first movement object based on the similarity scores.

20. A computing device for controlling a movement training environment, comprising:

a processing unit; and a memory containing instructions, that, when executed by the processing unit, cause the processing to:

retrieve a movement object from a plurality of movement objects stored in the memory, wherein the movement object comprises a first keyframe and first annotation data that includes auxiliary information corresponding to the first keyframe;

attain first motion capture data associated with a first user performing a movement based on the movement object;

generate a first articulable representation based on the first motion capture data;

compare at least one first joint position related to the first articulable representation with at least one second joint position related to a second articulable representation associated with the movement object;

calculate a first similarity score for the first keyframe based on a difference between the at least one first joint position and the at least one second joint position; and display the movement object, including the first annotation data, and the first similarity score on a display device.

* * * * *